(12) United States Patent
Mitsuhashi et al.

(10) Patent No.: US 9,012,615 B2
(45) Date of Patent: Apr. 21, 2015

(54) METHODS FOR CHARACTERIZING KIDNEY FUNCTION

(71) Applicants: Hitachi Chemical Company, Ltd., Tokyo (JP); Hitachi Chemical Research Center, Inc., Irvine, CA (US); City of Sapporo, Sapporo (JP)

(72) Inventors: Masato Mitsuhashi, Irvine, CA (US); Hiroshi Harada, Hokkaido (JP)

(73) Assignees: Hitachi Chemical Company, Ltd, Tokyo (JP); Hitachi Chemical Research Center, Inc., Irvine, CA (US); City of Sapporo, Sapporo (JP)

( * ) Notice: Subject to any disclaimer, the term of this patent is extended or adjusted under 35 U.S.C. 154(b) by 0 days.

(21) Appl. No.: 13/710,237

(22) Filed: Dec. 10, 2012

(65) Prior Publication Data

US 2013/0089864 A1 Apr. 11, 2013

Related U.S. Application Data

(63) Continuation-in-part of application No. PCT/US2011/040057, filed on Jun. 10, 2011.

(60) Provisional application No. 61/354,098, filed on Jun. 11, 2010.

(51) Int. Cl.
*C12Q 1/68* (2006.01)
*A01N 43/04* (2006.01)

(52) U.S. Cl.
CPC ........ *C12Q 1/6809* (2013.01); *C12Q 2525/207* (2013.01); *C12Q 2600/178* (2013.01); *C12Q 1/6883* (2013.01); *C12Q 2600/158* (2013.01); *C12Q 2600/142* (2013.01)

(58) Field of Classification Search
CPC ........ C12Q 1/68; C12Q 1/6837; C12Q 1/686; C12Q 1/6844; C12Q 1/6846
See application file for complete search history.

(56) References Cited

U.S. PATENT DOCUMENTS

| | | | |
|---|---|---|---|
| 4,925,572 A | 5/1990 | Pall | |
| 5,747,256 A | 5/1998 | Yan et al. | |
| 6,329,179 B1 | 12/2001 | Kopreski | |
| 6,964,850 B2 | 11/2005 | Bevilacqua et al. | |
| 7,741,023 B2 | 6/2010 | Mitsuhashi | |
| 2004/0029124 A1 | 2/2004 | Zohlnhofer et al. | |
| 2004/0072193 A1 | 4/2004 | Mitsuhashi | |
| 2004/0203037 A1 | 10/2004 | Lo et al. | |
| 2004/0265864 A1 | 12/2004 | Mitsuhashi | |
| 2007/0254351 A1 | 11/2007 | Abrignani et al. | |
| 2008/0009009 A1 | 1/2008 | Mitsuhashi | |
| 2008/0015162 A1* | 1/2008 | Bhanot et al. | 514/44 |
| 2008/0268429 A1 | 10/2008 | Pietrzkowski | |
| 2009/0011410 A1 | 1/2009 | Mitsuhashi | |
| 2009/0023149 A1 | 1/2009 | Knudsen | |
| 2009/0149333 A1 | 6/2009 | Knudsen et al. | |
| 2010/0113290 A1 | 5/2010 | Klass et al. | |
| 2010/0196426 A1* | 8/2010 | Skog et al. | 424/400 |
| 2013/0089855 A1 | 4/2013 | Mitsuhashi | |
| 2013/0172208 A1 | 7/2013 | Mitsuhashi | |
| 2013/0337462 A1 | 12/2013 | Mergemeier | |

FOREIGN PATENT DOCUMENTS

| | | |
|---|---|---|
| WO | 2006/045053 | 4/2006 |
| WO | WO-2008/092993 A1 * | 8/2008 |
| WO | 2009/015357 | 1/2009 |
| WO | 2010/056337 | 5/2010 |
| WO | 2010/086163 | 8/2010 |
| WO | 2011/156734 | 12/2011 |
| WO | 2011/156763 | 12/2011 |

OTHER PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111 at pp. 81-82.*
Lescuyer et al, Proteomics: Clinical Applications 2 (7-8): 1008 (2008).*
Cutillas et al., The urinary proteome in Fanconi syndrome implies specificity in the reabsorption of proteins by renal proximal tubule cells., Am. J. Physiol. Renal Physiol., vol. 287(3):F353-364 (2004).
Hashem, Biochemical and expression studies on Acquaporin 9 (AQP9) in wild and AQP9 knockout mice, Veterinarski Archie, vol. 80(1):93-112 (2010).
Hewitt et al., Discovery of Protein Biomarkers for Renal Diseases, J. Am. Soc. Nephrol., vol. 15(7): 1677-1689 (2004).
International Search Report and Written Opinion for PCT/US2011/040057, mailed Oct. 21, 2011.
Miranda et al., Nucleic acids within urinary exosomes/microvesicles are potential biomarkers for renal disease, Kidney International, vol. 78(2): 191-199 (Apr. 28, 2010).
Zefon International. Glass Fiber Filters, Jan. 14, 2010 [retreived from the internet Oct. 7, 2011; <http://web.archive.org/web/20100114112921/http://www.zefon.com/store/glass-fiber-filters/>].
Zhou et al., Urinary exosomal transcription factors, a new class of biomarkers for renal disease, Kidney International, vol. 74(5):613-621 (2008).
Chen et al. Microfluidic isolation and transcriptome analysis of serum microvesicles. The Journal of the Royal Society of Chemistry (2010), 10, pp. 505-511.
Cutillas et al., The urinary proteome in Fanconi syndrome implies specificity in the reabsorption of proteins by renal proximal tubule cells. Am J Physiol Renal Physiol 287:F353-F364, 2004.
Gene Cards DEFA3 Gene, first internet archive Aug. 7, 2010, p. 1-14.
Haas et al. Patient characteristics associated with successful mobilizing and autografting of peripheral blood progenitor cells in malignant lymphoma. Blood, vol. 83, No. 12 Jun. 15, 1994, pp. 3787-3794.
Hotfilder et al., Def-2, -3, -6 and -8, novel mouse genes differentially expressed in the haemopoietic system. British Journal of Haematology, 1999, 106, pp. 335-344.

(Continued)

*Primary Examiner* — James Martinell
(74) *Attorney, Agent, or Firm* — Knobbe Martens Olson & Bear, LLP

(57) ABSTRACT

Embodiments of the invention relate generally to methods of characterizing kidney function. In particular, several embodiments quantify kidney-associated marker RNA isolated from vesicles contained in patient urine samples. In some embodiments, the quantified RNA from urine vesicles is compared to a normal population and in some embodiments is compared to the patient to evaluate kidney function over time.

7 Claims, 13 Drawing Sheets

(56) References Cited

OTHER PUBLICATIONS

Ito et al. Myeloid Reconstruction. Serum stem cell growth factor for monitoring hematopoietic recovery following stem cell transplantation. Bone Marrow transplantation (2003) 32, pp. 391-398.

Jimenez et al., "Endothelial micropadicles released in thrombotic thrombocytopenic purpura express von Willibrand factor and markers of endothelial activation," Br J Haemat, Dec. 2003, 123(5):896-902.

Labsource: Whatman Glass Microfiber Filters 2009. [Retrived from internet Dec. 12, 2011:<URL:http://www.labsource.com/Catalog/Group.aspx?GroupID=82>] p. 1.

Tomblyn et al., Guidelines for preventing infectious complications among hematopoietic cell transplantation recipients: A global prespective. Biol Blood Marrow Transplant, 15: 1143-1238 (2009).

Xu et al. Gene expression in peripheral blood differs after cardioembolic compared with large—vessel atherosclerotic stroke: biomarkers for the etiology of ischemic stroke. J Cereb Blood Flow & Metab. 28: 1320-1328 (2008).

Wellmann et al., Detection of differentially expressed genes in lymphomas using cDNA arrays; identification of clusterin as a new diagnostic marker for anaplastic large-cell lymphomas. Blood, Jul. 15, 2000, 96(2), pp. 398-404.

Zucker et al., Immature platelet fraction as a predictor of platelet recovery following hematopoietic progenitor cell transplantation. Laboratory Hematology, 2006, 12, pp. 125-130.

International Preliminary Report on Patentability, re PCT Application No. PCT/US2011/40015, mailed Dec. 27, 2012.

International Search Report and Written Opinion, re PCT Application No. PCT/US2011/40015, mailed Jan. 5, 2012.

Japanese Office Action, re JP Application No. 2013-514399, dated Aug. 12, 2014.

* cited by examiner

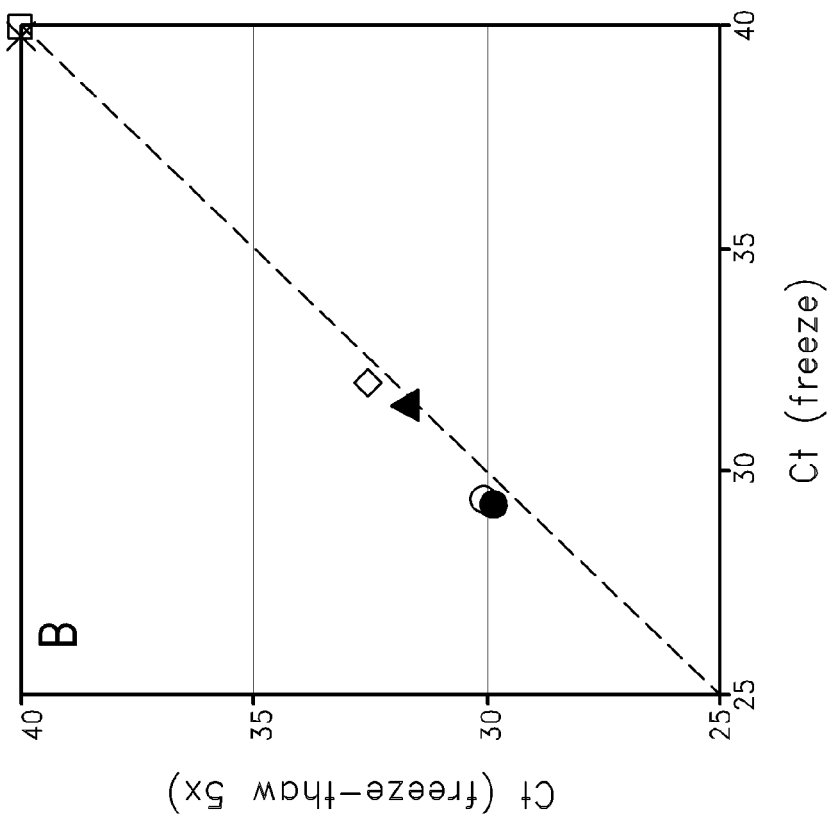
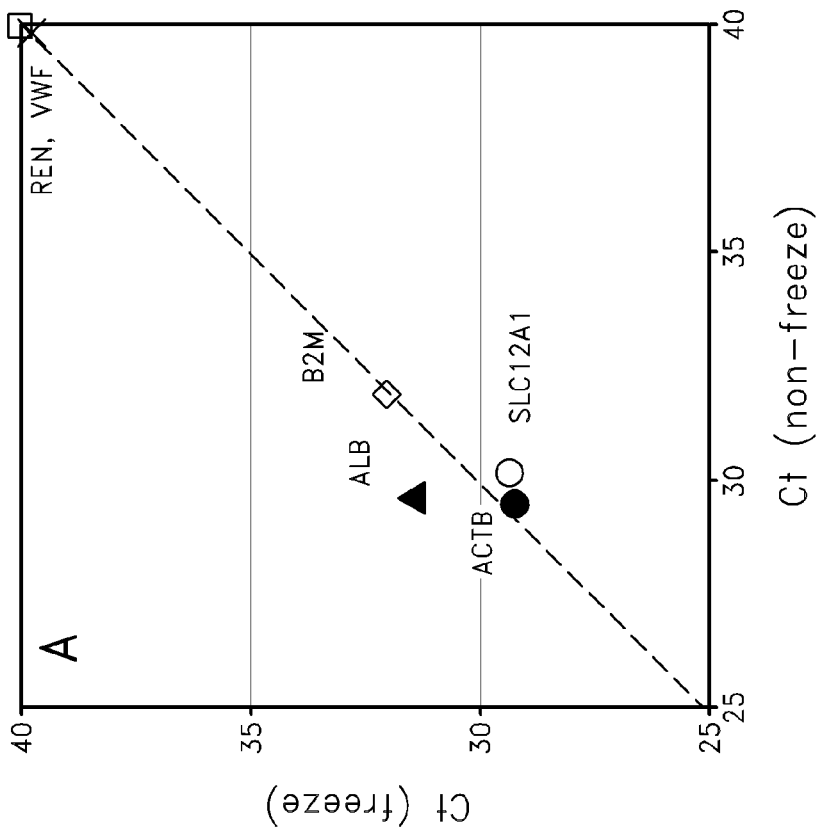
*FIG. 3A*
*FIG. 3B*

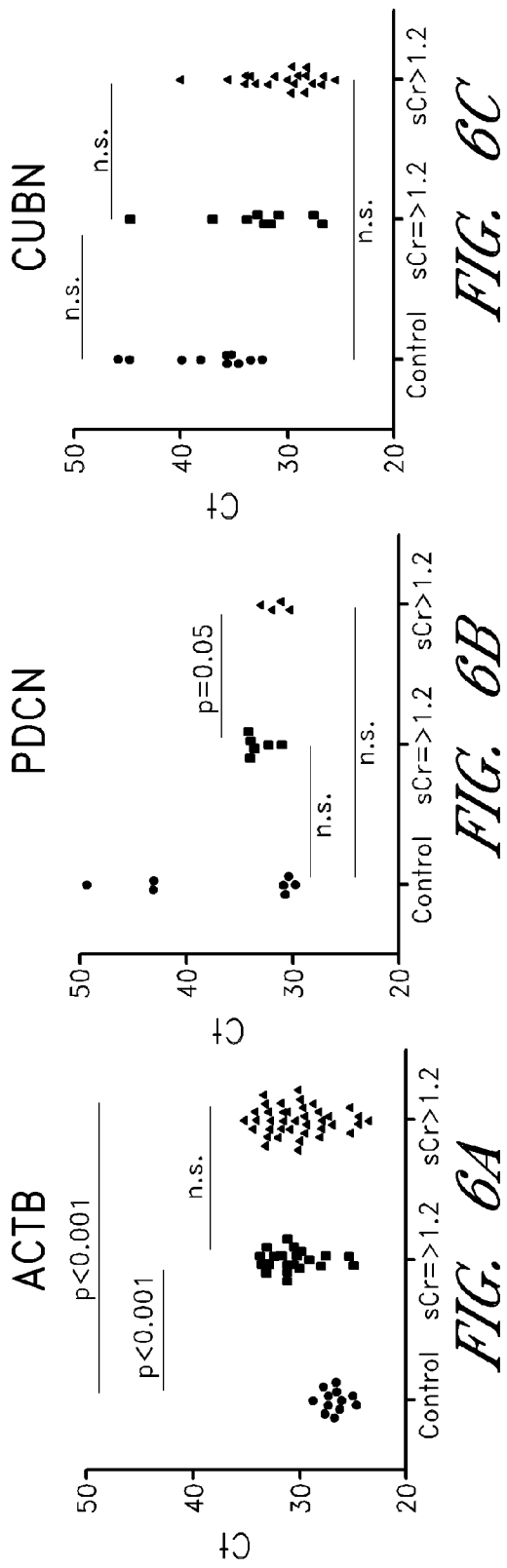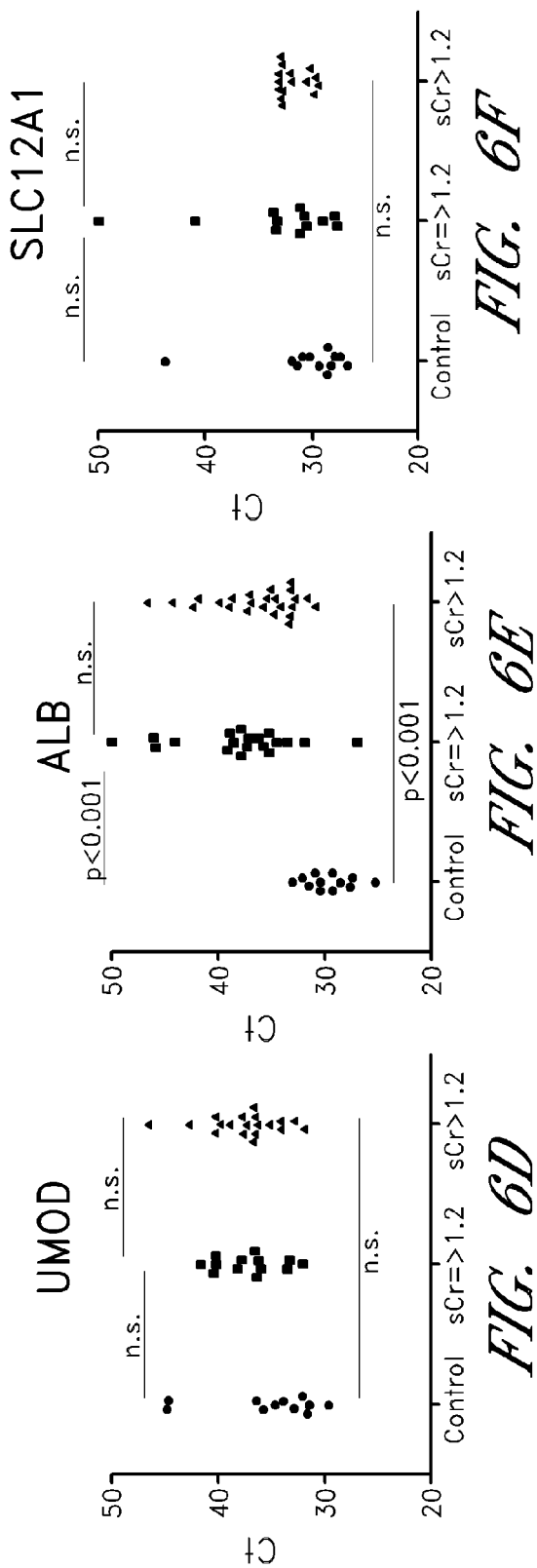

METHODS FOR CHARACTERIZING KIDNEY FUNCTION

This invention was made pursuant to a Joint Research Agreement between Hitachi Chemical Research Center, Inc. and the Sapporo City General Hospital.

RELATED CASES

The contents of each priority document listed in the associated Application Data Sheet is incorporated in its entirety by reference herein. This application also incorporates by reference the sequence listing submitted as ASCII text filed concurrently via EFS-Web. The Sequence Listing is provided as a file entitled "ST25 Sequence Listing—HITACHI.102P1", created on Dec. 6, 2012 and which is 8.0 kilobytes in size.

BACKGROUND OF THE INVENTION

1. Field of the Invention

The present disclosure relates to methods for the characterization of kidney function. Several embodiments relate to the diagnosis of kidney disease and more specifically, the present disclosure relates to the field of characterizing by quantifying kidney-related RNA contained in vesicles to characterize kidney function.

2. Description of Related Art

In many cases, physicians interpret a patient's symptoms, medical history and the results of a physical exam to derive an initial diagnosis. Medical tests are an integral part of confirming or modifying an initial diagnosis. Currently, some diagnostic medical tests are performed on blood extracted from a patient to determine disease from a biochemical pattern that is not present in healthy patients or is altered from a previously obtained patient sample. These tests commonly utilize plasma or serum and measure, for example electrolytes, urea, creatinine, and glucose. Other tests measure plasma proteins such as albumins, immunoglobulins, fibrinogens, and regulatory proteins. Still other tests measure other biological compounds, such as, for example, thiamin, riboflavin, niacin, vitamin B6, folic acid, vitamin D, biotin, iron, and clotting factors factor V and factor X.

Similarly, in the context of evaluating kidney function, measurement of the plasma concentrations of waste substances that should be removed by a functional kidney (such as creatinine and urea) or concentrations of electrolytes are often made to determine renal function. However, blood urea and creatinine levels often will not be raised above the normal range until a substantial amount (e.g., 40% or greater) of total kidney function is lost. Evaluation of glomerular filtration rate (GFR) or clearance of pharmacological marker compounds can also be used to evaluate kidney function. Analysis of 24 hour urine samples can also be used to evaluate kidney function. Another prognostic marker for kidney function is proteinuria, an elevated level of protein in the urine. Increasing amounts of proteins (such as albumin) in the urine indicate progressively increasing amounts of kidney damage, and associated loss of function.

However, these diagnostic tests are typically antibody based tests, commonly an ELISA, which may have limitations with respect to sensitivity. The combination of questionable assay accuracy at low assay target concentration ranges with the presumably low levels of creatinine (or other assay target) in the early stages of disease make it possible that diagnosis in early disease stages is not made. Additionally, certain diagnostic tests employ chemical reactions (e.g., colorimetric changes) to identify markers from blood or other fluid samples. Such tests may also be affected by similar limitations as are described above. Thus, there exists a need for a sensitive, accurate and reproducible diagnostic test for evaluating kidney function that enable early detection and/or diagnosis of compromised kidney function.

SUMMARY

Based on these needs, there is provided herein a method for enabling a medical professional to recommend or not recommend a therapy to a subject based on the kidney function of the patient, the method comprising, obtaining a first sample of urine from a patient, wherein the sample comprises vesicles that are associated with RNA, capturing the vesicles from the first urine sample, lysing the vesicles to release the vesicle-associated RNA, wherein the vesicle-associated RNA comprises an RNA associated with kidney function, quantifying the RNA associated with kidney function, comparing the amount of the RNA associated with kidney function from the patient to the quantity of a corresponding RNA from individuals having normal kidney function, wherein a difference in the quantity of the RNA associated with kidney function between the patient and the individuals indicates a change in kidney function of the patient, and wherein a lack of a difference in the quantity of the RNA associated with kidney function between the patient and the individuals indicates that the kidney function of the patient is normal; and 1) indicating to the medical professional when there is a change in the kidney function of the patient, or 2) indicating to the medical professional when the kidney function of patient is normal, thereby enabling a medical professional to recommend a therapy or forego recommending a therapy to the patient based on the kidney function of the patient.

In several embodiments, there is also provided a method for enabling a medical professional to recommend a region-specific kidney therapy to a patient based on the kidney function of the patient, the method comprising obtaining a first sample of urine from a patient, wherein the sample comprises vesicles that are associated with RNA, capturing the vesicles from the first urine sample, lysing the vesicles to release the vesicle-associated RNA, wherein the vesicle-associated RNA comprises an RNA associated with kidney function, quantifying the RNA associated with kidney function, wherein the RNA is obtained from a specific region of the kidney and/or is associated with the function of a specific region of the kidney, comparing the amount of the RNA associated with kidney function from the patient to the quantity of a corresponding RNA from individuals having normal kidney function, wherein a difference in the quantity of the RNA associated with kidney function between the patient and the individuals indicates a change in kidney function of the patient, and wherein a lack of a difference in the quantity of the RNA associated with kidney function between the patient and the individuals indicates that the kidney function of the patient is normal; and 1) indicating to the medical professional when the kidney function of the patient is normal, thereby enabling a medical professional to recommend a therapy or forego recommending a therapy to the patient based on the kidney function of the patient; or 2) indicating to the medical professional when there is a change in the kidney function of the patient and indicating to the medical professional the specific region of the kidney having a change in function, thereby enabling the medical professional to recommend a region-specific kidney therapy.

In several embodiments, there is provided a method for advising a subject to undertake a therapy based on the subject's kidney function, the method comprising, ordering a test of a urine sample from the subject, the test comprising, obtaining a first sample of urine from a patient, wherein the sample comprises vesicles that are associated with RNA, capturing the vesicles from the first urine sample, lysing the vesicles to release the vesicle-associated RNA, wherein the vesicle-associated RNA comprises an RNA associated with kidney function, quantifying the RNA associated with kidney function, comparing the amount of the RNA associated with kidney function from the patient to the quantity of a corresponding RNA from individuals having normal kidney function, wherein a difference in the quantity of the RNA associated with kidney function between the patient and the individuals indicates a change in kidney function of the patient, and wherein a lack of a difference in the quantity of the RNA associated with kidney function between the patient and the individuals indicates that the kidney function of the patient is normal; and advising the subject to undergo a therapy when there is a change in the subject's kidney function or advising the subject to forego a therapy when there is not a change in the subject's kidney function.

In several embodiments, capturing the vesicles comprises filtering the urine sample in order to trap the vesicles on the filter. In several embodiments, the lysing is performed while the vesicles are trapped on the filter. In several embodiments, the methods further comprise centrifuging the sample to remove cellular debris and filtering the supernatant of the centrifuged urine.

In several embodiments, the quantification is performed by a method selected from the group consisting of reverse-transcription polymerase chain reaction (RT-PCR), real-time RT-PCR, northern blotting, fluorescence activated cell sorting, ELISA, and mass spectrometry. In one embodiment, the quantifying comprises amplifying the RNA using RT-PCR. In several embodiments, the RNA comprises poly(A)+ RNA.

In several embodiments, the kidney function is altered due to disease, the disease selected from the group consisting of chronic kidney disease, acute renal failure, diabetic nephropathy, glomerulonephritis, glomerulosclerosis, focal segmental glomerulosclerosis, membranous nephropathy, minimal change disease, and kidney disease secondary to other diseases such as atherosclerosis, hypertension, cardiovascular diseases, obesity, hypercholesterolemia, diabetes, collagen diseases, autoimmune disease, and infection. In some embodiments, the kidney function is altered due to administration of a pharmacological agent to the patient.

In several embodiments, there are also provided methods for characterizing kidney function comprising obtaining a sample of urine from a patient, wherein the sample comprises vesicles that are associated with RNA, capturing the vesicles from the sample, lysing the vesicles to release the vesicle-associated RNA, wherein the vesicle-associated RNA comprises an RNA associated with kidney function, quantifying the RNA associated with kidney function; and comparing the amount of the RNA associated with kidney function from the patient to the quantity of a corresponding RNA from individuals having normal kidney function, wherein a difference in the quantity of the RNA associated with kidney function between the patient and the individuals indicates a change in kidney function of the patient.

In several embodiments, isolating the vesicles from the sample comprises filtering the urine. In some embodiments, the filtration traps the vesicles on the filter. In several embodiments, the lysing is performed while the vesicles are trapped on the filter.

In several embodiments, the method further comprises centrifuging the sample to remove cellular debris. In one embodiment, the centrifugation is performed prior to isolating the vesicles. In several embodiments, the concentrating the vesicles further comprises filtering the supernatant of the centrifuged urine.

In several embodiments, quantifying comprises amplifying the RNA using PCR.

In several embodiments, the kidney function is altered due to kidney damage. In some embodiments, the kidney damage comprises one or more of damage to the glomerulus, damage to the endothelium, damage to the proximal tubule, damage to the loop of Henle, damage to the collecting duct, and damage to the ureter.

In several embodiments, the RNA associated with kidney function is selected from the group consisting SLC12A1, UMOD, vWF, MMP1, MMP3, SLC22A6, SLC22A 8, SLC22A 12, podocin, cubulin, LRP2, AQP9, and albumin. In one embodiment, the RNA associated with kidney function is SLC12A1.

In several embodiments, the kidney function is altered due to changes in blood flow into or out of the kidney. In several embodiments, the kidney function is altered due to disease. In several embodiments, the disease is selected from the group consisting of chronic kidney disease, acute renal failure, diabetic nephropathy, glomerulonephritis, glomerulosclerosis, focal segmental glomerulosclerosis, membranous nephropathy, minimal change disease, and kidney disease secondary to other diseases such as atherosclerosis, hypertension, cardiovascular diseases, obesity, hypercholesterolemia, diabetes, collagen diseases, autoimmune disease, and infection.

In several embodiments, the kidney function is altered due to administration of a pharmacological agent to the patient. In some embodiments, the pharmacological agent is administered to the patient to treat a disease.

In several embodiments, the RNA associated with kidney function is obtained from a specific region of the kidney. In several embodiments, the RNA associated with kidney function is associated with the function of a specific region of the kidney. In several embodiments, the specific region of the kidney comprises the glomerulus. In several embodiments, the specific region of the kidney comprises the proximal tubule. In several embodiments, the specific region of the kidney comprises the distal tubule.

In several embodiments, the vesicles are isolated by a method comprising loading at least a portion of the first sample of urine into a sample loading region of a vesicle capture device, passing the urine from the sample loading region through a vesicle-capture material in the vesicle capture device, the vesicle-capture material comprising glass-like materials to produce a supernatant, passing the supernatant to a sample receiving region of the vesicle capture device and discarding the supernatant, wherein the passings result in capture of the vesicles from the urine sample on or in the vesicle-capture material, thereby capturing the vesicles.

In some embodiments, the vesicle-capture material comprises a plurality of layers of the material. In several embodiments the plurality of layers of the vesicle-capture material comprises at least a first layer and a second layer of glassfiber. In several embodiments, the biological fluid is passed through the first layer of glassfiber so as to capture material from the biological sample that is about 1.6 microns or greater in diameter. In several embodiments, the biological fluid is passed through the second layer of glassfiber so as to capture vesicles having a minimum size from about 0.6 microns to about 0.8 microns in diameter, and having a maximum size of less than 1.6 microns.

There is also provided herein a method for characterizing kidney function comprising obtaining at least two samples of urine from a patient, wherein the samples comprise vesicles that are associated with RNA, isolating the vesicles from the samples, lysing the vesicles to release the vesicle-associated RNA, wherein the vesicle-associated RNA comprises an RNA associated with kidney function and an RNA that does not change in response to kidney function, quantifying the RNA associated with kidney function and the RNA that does not change in response to kidney function; and determining a ratio between the amount of the RNA associated with kidney function from the patient and the quantity of an RNA that does not change in response to kidney function, wherein a difference in the ratio between the two or more urine samples indicates a change in kidney function of the patient.

In one embodiment, the RNA that does not change in response to kidney function is one of beta-actin or beta-2-microglobulin.

In several embodiments, there is also provided a nucleic acid based method of detecting alterations in kidney function, comprising obtaining a sample of urine from a patient, wherein the urine sample comprises cellular debris and vesicles that are associated with RNA, separating the vesicles from the cellular debris, lysing the vesicles to yield a lysate comprising RNA associated with kidney function; and quantifying the RNA associated with kidney function, wherein an increase or a decrease of the amount of the RNA from the urine sample as compared to the amount normally found in urine is correlated with altered kidney function in the patient.

BRIEF DESCRIPTION OF THE FIGURES

FIGS. 3A-3C depicts the effects of freeze-thaw cycles on urine.

FIGS. 6A-6H depict a comparison of the expression of positively detected kidney-function associated mRNAs in a control group and two groups of post-transplant patients (separated based on serum creatinine concentration).

FIGS. 7A-7C depict the mRNA expression data normalized to the expression of albumin. FIGS. 7D-7F depict the mRNA expression data normalized to the expression of beta-actin.

DETAILED DESCRIPTION

General

Figure 1B:
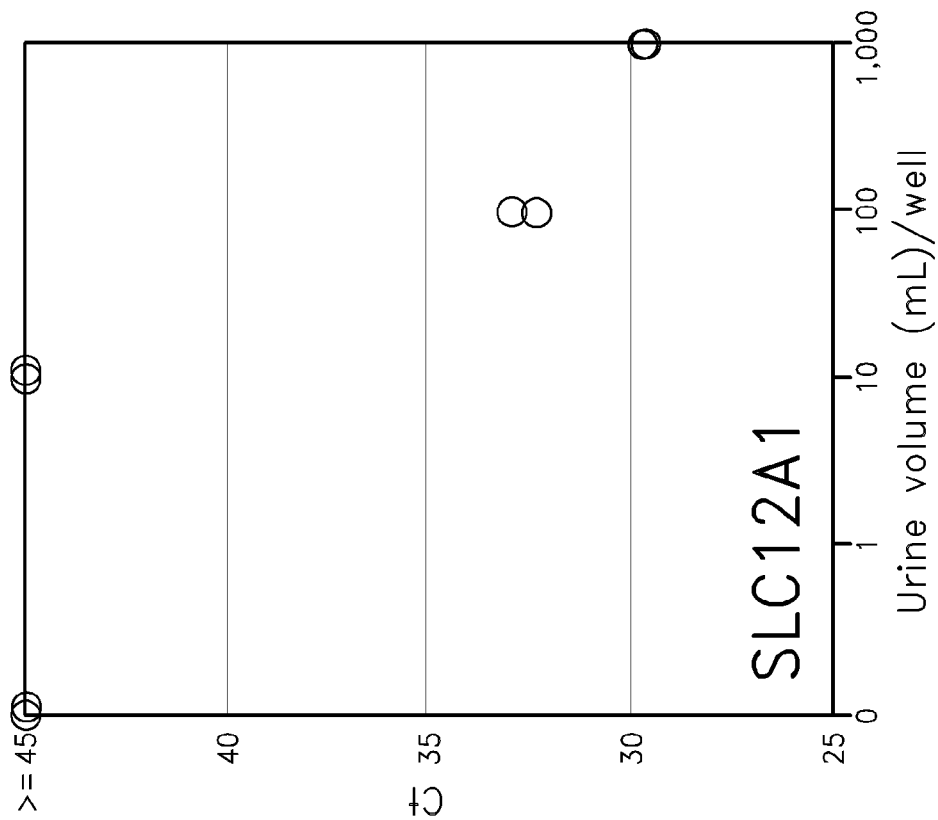
FIGS. 1A-1B depicts analysis of urine volume.

A physician's diagnosis is typically based upon the medical history of the patient as well as current symptoms. In addition to a physical examination that may expose signs of the underlying disease, diagnostic tests may be ordered to confirm an initial diagnosis. Evaluation of kidney function presents a unique situation for diagnostic analysis, as the function of the organ to produce urine, the composition of which results is reflected with concentration changes of compounds in the blood. Thus kidney function can be evaluated using two fluids, urine and/or blood.

Many diagnostic tests are directed to detecting certain proteins in the fluid. However, protein-based assays, while efficient at certain target concentrations, may suffer from lack of sensitivity at low target concentrations. Diagnostic techniques based on nucleic acid detection offer an alternative to protein detection that, in many cases, provides a higher degree of sensitivity. Nucleic acid can be isolated from cells that are obtained from a blood or urine sample, but also exist extracellularly. While several embodiments disclosed herein are directed to the isolation of RNA associated with vesicles present in patient urine samples, in several embodiments, RNA (and the associated markers) that are normally found in blood or plasma are isolated from urine samples. In some embodiments, these blood-borne markers are present in the urine due to damage or disease of the kidney that has compromised the normal blood filtering function of the kidney.

Loss of kidney function is progressive in nature and some markers of loss of function or disease may not be detected by traditional diagnostic methods until the disease is well-established. In such cases, as the kidney disease progresses, the prognosis becomes increasingly poor. As such, early detection of the kidney disease may lead to easier treatment regimes and possibly a significantly improved patient outcome. Thus, there is a need for a more sensitive alternative to the diagnostic tests currently used in the detection and characterization of the early stages of kidney diseases or loss of function.

Vesicle-Associated RNA

In several embodiments disclosed herein, there are provided methods for the capture of RNA from a sample of patient body fluid and subsequent analysis of that RNA for disease and/or tissue specific markers. In several embodiments, the method comprises isolated of vesicles associated with RNA from a patient urine sample. In other embodiments, vesicles are obtained from plasma, serum, cerebrospinal fluid, sputum, saliva, mucus, tears etc. Many diagnostic tests are designed around using a small patient fluid sample, and in some embodiments, a small amount (e.g. 15-50 mL of urine) is used. However, several embodiments are particularly advantageous because large volumes of patient urine are readily available.

In several embodiments, a sample of urine obtained from a patient is evaluated for nucleic acids associated with the kidney and/or kidney function. As described below, in some embodiments, the nucleic acids are vesicle-associated. In some embodiments, the nucleic acids detected are indicative of kidney disease and/or function. In some embodiments, this is because the nucleic acids are not normally present in the urine. In some embodiments, the nucleic acids detected are indicative of kidney disease and/or function because the nucleic acids are present in the patient urine sample at a greater or lesser concentration as compared to a population of individuals known to have normal kidney function (e.g., a control group). In some embodiments, urine is collected and nucleic acids are evaluated over time (e.g., to monitor a patient's response to therapy or disease progression).

According to various embodiments, various methods to quantify mRNA are used, including Northern blot analysis, RNAse protection assay, PCR, nucleic acid sequence-based amplification, branched-DNA amplification, and DNA or RNA microarray analysis. Additionally, in some embodiments, vesicle associated RNA may be analyzed using Chip-Sequencing, which combines chromatin immunoprecipitation with nucleic acid sequencing to identify protein-nucleic acid interactions.

While RNA typically is contained in the intracellular environment, RNA also exists extracellularly. In some cases, the RNA is naked (e.g., not encapsulated or associated with another structure or compound. RNAses, which degrade RNA, are known to be elevated in some disease states, for example, in certain cancers. The extracellular environment, including the plasma, serum, or urine, is known to contain substantial quantities of RNAses. Given this context, extracellular RNA is often considered a meaningless degradation product an extracellular sample, not only because its levels may not be representative of the true levels of the intracellular message, but also due to the instability and poor quality of the RNA. However, in some cases, RNA is associated with extracellular vesicles. In several embodiments, diagnosis and characterization of kidney disease/function is performed by detection and quantification of specific RNA species from RNA-containing vesicles isolated from patient samples (e.g., urine). In some embodiments, such vesicles are trapped on a filter, thereby allowing RNA extraction from the vesicles.

Due to the rapid rate of RNA degradation in the extracellular environment, conventional understanding suggests that many tissues are unable to provide extracellular RNA suitable as a diagnostic target, because such RNA would be degraded before it could be used as a template for detection. However, Applicant has unexpectedly discovered that extracellular RNA, when evaluated according to several of the methods disclosed herein, advantageously allows for the detection of kidney specific markers reflective of kidney function or disease from extracellular vesicles in patient urine samples.

Extracellular RNA is often associated with one or more different types of membrane particles (ranging in size from 50-80 nm), exosomes (ranging in size from 50-100 nm), exosome-like vesicles (ranging in size from 20-50 nm), and microvesicles (ranging in size from 100-1000 nm). In several embodiments, these vesicles are isolated and/or concentrated, thereby preserving vesicle associated RNA despite the high RNAse extracellular environment. In several embodiments, these techniques utilized this unexpected source of high quality RNA to increase the sensitivity of diagnostic methods.

Even after the recognition that some RNA is vesicle associated, many RNA purification techniques have not been adapted to efficiently capture and preserve vesicle associated RNA. Often, samples are separated by centrifugation on a density gradient to fractionate the non-cellular portion of the sample. In some cases, this is followed by high speed centrifugation to cause vesicle sedimentation or pelleting. Such approaches are time consuming and may require expensive and specialized equipment as compared to the format used in certain embodiments disclosed herein. Moreover, in some cases, RNA may be damaged by the high pressures that accompanying ultracentrifugation. In several embodiments, the methods described herein are rapid, inexpensive, highly reproducible, and have low variability between replicated measurements. Moreover, several embodiments are particularly advantageous in that they do not require lengthy protocols that risk RNA degradation.

In several embodiments, the methods and apparatus described herein employ different types of filters to capture vesicles of different sizes. In some embodiments, differential capture of vesicles is made based on the surface expression of protein markers. By having a filter that is reactive to a specific surface marker, such as a filter coupled to an antibody that binds a marker on the surface of the vesicle, specific types of vesicles or vesicles of different origins are isolated. In some embodiments, the markers are unique vesicle proteins or peptides. In some disease states, the markers may also comprise certain modifications, which, in some embodiments, are used to isolate particular vesicles. Modification may include, but are not limited to addition of lipids, carbohydrates, and other molecules such as acylated, formylated, lipoylated, myristolylated, palmitoylated, alkylated, methylated, isoprenylated, prenylated, amidated, glycosylated, hydroxylated, iodinated, adenylated, phosphorylated, sulfated, and selenoylated, ubiquitinated. In some embodiments, the vesicle markers comprise non-proteins such as lipids, carbohydrates, nucleic acids, RNA, DNA, etc.

In several embodiments, the specific capture of vesicles based on their surface markers also enables a "dip stick" format where each different type of vesicle is captured by dipping probes coated with different capture molecules (e.g., antibodies with different specificities) into a patient urine sample.

Kidney Structure, Function, and Disease

A human kidney has a generally bean-shaped structure, and each kidney has concave and convex surfaces. The renal hilum is the concave surface and is the point at which the renal artery enters the kidney, and the renal vein and ureter leave. The interior anatomy of the kidney is divided into two main structures (tissue types), the renal cortex (the superficial area) and the renal medulla (the more interior area). Nephrons, which are functional unit of the kidney span the cortex and medulla. The initial filtering portion of a nephron is the renal corpuscle, located in the cortex, which is followed by a renal tubule that passes from the cortex deep into the medulla.

The renal corpuscle comprises the glomerulus, which performs the first step in filtering blood to form urine and Bowman's capsule, which surrounds the glomerulus. In contrast to most other capillary beds, the glomerulus drains into an efferent arteriole rather than a venule, which results in a high back-pressure in the glomerulus. This high pressure in the glomerulus aids in of ultrafiltration, where fluids and soluble materials in the blood are forced out of the capillaries and into Bowman's capsule. This high pressure also has the potential to lead to kidney damage in certain disease states. For example, in diabetes the elevated level of glucose, a relatively large solute in the blood, may cause physical damage to the glomerulus. This initial damage may be further exacerbated by additional periods of high blood glucose, as elevated glucose levels appear to increase the speed of blood flow into the kidney, putting a further strain on the filtering glomeruli and raising blood pressure.

After passing through the glomerulus, filtrate passes through the proximal tubule, the loop of Henle, the distal convoluted tubule, and the collecting duct. In sum, these anatomical structures function to generate a concentration gradient from the cortex to the medulla, which allows for the reabsorption of water from the filtrate, which creates concentrated urine for excretion.

The kidneys are essential elements of the urinary system and also serve homeostatic functions such as the regulation of electrolytes, maintenance of acid-base balance, and regulation of blood pressure. Kidney function, broadly speaking, is to filter the blood and secrete various toxins, metabolic waste products, and/or reabsorb certain nutrients, amino acids, and water. Water reabosrption is a key function, as the healthy kidney generates about 2 liters of urine from about 180 liters of filtrate each day. In addition, the kidney is involved in regulation of acid-base balance and electrolyte concentrations, regulating extracellular fluid volume, and regulation of blood pressure. These diverse kidney functions are accomplished by way of the filtration function of the kidney, as well as through integration with the endocrine system. The kidney is responsive to, or produces, a variety of hormones, including renin, angiotensin II, aldosterone, antidiuretic hormone, and atrial natriuretic peptide, among others.

Common clinical conditions involving the kidney include nephritic (damage to glomerulus specifically) and nephritic (damage to kidney generally) syndromes, renal cysts, acute kidney injury, chronic kidney disease, urinary tract infection, nephrolithiasis (kidney stones), and urinary tract obstruction.

Various cancers of the kidney exist, including, but not limited to, renal cell carcinoma, Wilms tumor, and renal cell carcinoma.

Several embodiments described herein are advantageous because markers associated with kidney function and/or disease can be rapidly assessed in a high through put protocol. Such sampling approach is difficult with traditional purification techniques that require ultracentrifugation or other specialized and/or extensive isolation procedures. Several embodiments are used to diagnose and/or monitor various kidney diseases (or loss of function related thereto), including, but not limited to chronic kidney disease, acute renal failure, diabetic nephropathy, glomerulonephritis, glomerulosclerosis, focal segmental glomerulosclerosis, membranous nephropathy, minimal change disease, and kidney disease secondary to other diseases such as atherosclerosis, hypertension, cardiovascular diseases, obesity, hypercholesterolemia, diabetes, collagen diseases, as well as kidney damage caused by pharmaceuticals or other compounds.

In several embodiments, damage to the kidney vasculature, in particular, the endothelium of renal blood vessels is detected by evaluation of kidney endothelial cell-specific mRNA is a target for diagnosis in some embodiments. In some embodiments of the invention the markers are related to blood homeostasis such as endothelia cell marker von Willebrand factor (VWF), thrombin, factor VIII, plasmin, and fibrin. Von Willebrand factor is a plasma glycoprotein that is a mediator of platelet adhesion, as such it is released when the endothelium is damaged. VWF is involved in platelet aggregation and thrombus formation. In some embodiments, the markers may be kidney markers, such as, for example, Tamm-Horsfall glycoprotein (THP) also known as uromodulin, renin, solute carrier transporters (including, among others, SLC12A1, SLC22A6, SLC22A8, and SLC22A12), uromodulin associated kidney disease marker (UMOD), osteopontin (SPP1), and albumin (ALB), or kidney fibrosis markers, such as matrix metallopeptidase 1 (MMP1) and matrix metallopeptidase 3 (MMP3).

In some embodiments, marker RNA isolated from urine vesicles is indicative of kidney cancer. Such markers include, in some embodiments, carcinoembryonic antigen (CEA), mucin, alpha-fetoprotein, tyrosinase, melanoma associated antigen, and mutated tumor protein 53, p21, PUMA, prostate-specific antigen (PSA) or thyroglobulin. By quantifying the level of cancer associated-RNA from the urine vesicles of a patient and comparing it with a known healthy range or standard the presence kidney cancers can be detected. Other kidney cancer markers known in the art are used in other embodiments.

Several embodiments of the methods disclosed herein provide unexpected advantages over existing diagnostic and monitoring methods. For example, some diagnostic tests for kidney disease require a kidney biopsy, which is typically performed via puncture of the organ with a needle. The biopsy technique has the associated risks such as uncontrolled bleeding and infection. The methods described herein provide an opportunity to non-invasively identify RNA which indicates kidney disease or characterizes kidney function. Several embodiments thus unexpectedly enable remote sampling and assessment of the kidney without the associated increase in patient risk.

In addition to directly detecting kidney disease, several embodiments of the methods disclosed herein are particularly advantageous because they are used to correlate a loss of kidney function (or symptoms thereof) with other diseases that are not kidney specific, but secondarily impact the kidney. For example, diabetes mellitus is characterized by high blood glucose levels and is a chronic disorder of fat, protein, and carbohydrate metabolism. As discussed above, elevate blood glucose levels can lead to kidney damage and eventual reduction in kidney function. In some cases, diabetes mellitus leads to development of or is associated with one or more types of cardiovascular disease, which can further exacerbate kidney damage. In a healthy individual with normal functioning metabolism, insulin is produced by beta cells of the pancreas. The subsequent insulin release enables cells to absorb glucose. In contrast, in a diseased state the cells do not absorb glucose and it accumulates in the blood. This may lead to complications and/or damage to the kidney, as well as complications such as cardiovascular disease (coronary artery disease, peripheral vascular disease, and hypertension). Depending on the type of diabetes, a patient with diabetes either does not produce enough insulin or their cells do not properly respond to the insulin that their body does produce. In many cases, pre-diabetic individuals and/or those with diabetes live with early symptoms that are dismissed as being associated with other aspects of their lives or health. For example, post-prandial nausea may be ignored as heartburn, when in fact, the symptom is attributable to elevated blood glucose levels. Ignoring such symptoms over time can lead to, among other symptoms, excessive kidney damage prior to actual diagnosis. In several embodiments, the methods disclosed herein can be implemented in routine physical examinations to detect early markers of kidney damage due to diabetes before the symptoms become so severe that irreversible kidney damage is already sustained.

Other diseases may lead to secondary kidney damage which is detected by analysis of urine vesicles, according to several embodiments. Such diseases that cause secondary kidney damage include, for example, atherosclerosis, hypertension, obesity, hypercholesterolemia, hyperlipoproteinemia, hypertryglyceridemia, autoimmune diseases, infections (viral and/or bacterial).

For example, is several embodiments the impact of systemic disease on the kidney is characterized. Such systemic diseases include, but are not limited to systemic autoimmune diseases such as rheumatoid arthritis, systemic lupus erythematosus, Goodpasture's syndrome, IgA nephropathy, and systemic sclerosis. These diseases often result from an overactive immune response directed towards the patient's body. Detecting kidney damage, disease or loss of function is particularly beneficial, in some embodiments, some of these diseases, such as systemic lupus erythematosus, are characterized by a progressive immune attack on the body's cells and tissues, thereby leading to progressively greater damage tissues such as the kidneys. Thus, several embodiments are advantageous as detection of mild kidney effects early in the disease process may help prevent more devastating tissue damage.

In several embodiments, infections in other parts of the body can lead to kidney disease. In some embodiments, the methods disclosed herein are used to detect acute post-streptococcal glomerulonephritis (PSGN), which can occur after a Streptococcal infection (e.g., strep throat). In some embodiments, methods disclosed herein are used to detect kidney disease resulting from bacterial endocarditis, which is an infection of the tissues inside the heart, but is also associated with subsequent glomerular disease. Endocarditis sometimes leads to chronic kidney disease. In addition, in some embodiments, methods disclosed herein are used to detect kidney disease resulting from HIV infection.

In other embodiments, diagnosis of infectious disease is achieved by the detection of RNA or DNA from the infectious agent that is present in urine vesicles. In some embodiments the infectious agent may be severe acute respiratory syndrome (SARS)-associated coronavirus, influenza, and hepatitis C, influenza A, foot-and-mouth disease virus, Human bocavirus (HBoV) and also parasites like Trypanosoma brucei.

In several embodiments house keeping gene products or constitutively expressed gene products, or markers of basal cellular function can be used as markers or controls including glyceraldehyde 3-phosphate dehydrogenase, β actin (ACTB), and β2 microglobulin (B2M). Other housekeeping genes known in the art are used in other embodiments.

In several embodiments the disease and/or functional status of a patient's kidneys is monitored over time. In some embodiments, a first sample of urine is collected from a patient and the level of vesicle or particle associated RNA for a specific gene or genes is determined. A second or subsequent sample is collected from the patient and the level of specific RNA is determined. Any changes in kidney of the patient may thus be determined by comparing the first sample RNA level with the second sample RNA level or by comparing the samples to a control or standard. In some embodiments medication may have been administered to the patient before or after the collection of the first and/or second patient sample. In some embodiments, the medication may be a drug, nutritional supplement, vitamin, immunosuppressant, anti-inflammatory drug, anesthetic or analgesic, stem cell, graft, or kidney transplant. In some embodiments the monitoring may relate to a change in nutrition such as a reduction in caloric intake, or increased hydration, or change in exercise routine, or a change in sleeping pattern of the patient.

Methodology

Free extracellular RNA is quickly degraded by nucleases, making it a potentially poor diagnostic marker. As described above, some extracellular RNA is associated with particles or vesicles that can be found in urine. This vesicle associated RNA, which includes mRNA, is protected from the degradation processes in the urine. Microvesicles are shed from most cell types and consist of fragments of plasma membrane. Microvesicles contain RNA, mRNA, microRNA, and proteins and mirror the composition of the cell from which they are shed. Exosomes are small microvesicles secreted by a wide range of mammalian cells and are secreted under normal and pathological conditions. These vesicles contain certain proteins and RNA including mRNA and microRNA. Exosomes can also be released into urine by the kidneys and their detection may serve as a diagnostic tool, as described in several embodiments herein. In addition to urine, exosome-like vesicles may also be found in many body fluids such as blood, ascites and amniotic fluid, among others. Several embodiments evaluate nucleic acids such as small interfering RNA (saRNA), tRNA, and small activating RNA (saRNA), among others.

In several embodiments the RNA is used as a template to make complementary DNA (cDNA). In several embodiments, cDNA is amplified using the polymerase chain reaction (PCR). In other embodiments, amplification of nucleic acid and RNA may also be achieved by any suitable amplification technique such as nucleic acid based amplification (NASBA) or primer-dependent continuous amplification of nucleic acid, or ligase chain reaction.

In several embodiments, disease induces the expression of one or more markers, as measured by the amount of mRNA encoding said markers. In some embodiments urine is collected from a patient and directly evaluated. In other embodiments, urine vesicles are concentrated by trapping them on a filter. Isolated vesicles are then incubated with lysis buffer to release the RNA from the vesicles, the RNA then serving as a template for cDNA which is quantified with methods such as quantitative PCR (or other appropriate amplification technique). In several embodiments, the level of specific marker RNA from patient vesicles is compared with a desired control such as, for example, RNA levels from a healthy patient population, or the RNA level from an earlier time point from the same patient or a control gene from the same patient.

In some embodiments, the levels of mRNA encoding one or more markers will change significantly in a patient depending upon the presence or absence of disease. To determine these mRNA levels, in some embodiments, mRNA-containing vesicles are isolated from plasma using a device for isolating and amplifying mRNA. Embodiments of this device are described in more detail in U.S. patent application Ser. Nos. 10/796,298, 11/525,515, 11/376,018, 11/803,593, 11/803,594, and 11/803,663, each of which is incorporated in its entirety by reference herein.

Certain embodiments comprise a multi-well plate that contains a plurality of sample-delivery wells, a vesicle-capturing filter underneath the wells, and an mRNA capture zone underneath the filter which contains immobilized oligo(dT). In certain embodiments, the device also contains a vacuum box adapted to receive the filter plate to create a seal between the plate and the box, such that when vacuum pressure is applied, the urine is drawn from the sample-delivery wells across the vesicle-capturing filter, thereby capturing the vesicles and allowing non-vesicle urine components to be removed by washing the filters. In other embodiments, other means of drawing the urine samples through the sample wells and through across the vesicle-capturing filter, such as centrifugation or positive pressure, are used. In some embodiments of the device, vesicles are captured on a plurality of filter membranes that are layered together. In several embodiments, the captured vesicles are then lysed with a lysis buffer, thereby releasing mRNA from the captured vesicles. The mRNA is then hybridized to the oligo(dT)-immobilized in the mRNA capture zone. Further detail regarding the composition of lysis buffers that may be used in several embodiments can be found in U.S. patent application Ser. No.: 11/376,018, which is incorporated in its entirety by reference herein. In several embodiments, cDNA is synthesized from oligo(dT)-immobilized mRNA. In some embodiments, the cDNA is then amplified using real time PCR with primers specifically designed for amplification of disease-associated markers. Primers that are used in such embodiments are shown in Table 1. Further details about the PCR reactions used in some embodiments are also found in U.S. patent application Ser. No.: 11/376,018.

TABLE 1

Primer Sequences for RT-PCR Amplification

| Target | SEQ ID No: | FWD Sequence (5'-3') | SEQ ID No: | REV Sequence (3'-5') |
|---|---|---|---|---|
| B-Actin | 1 | CCTGGCACCCAGCACAAT | 2 | GCCGATCCACACGGAGTACT |
| B-2 microglobulin (B2M) | 3 | TGACTTTGTCACAGCCCAAGATA | 4 | AATGCGGCATCTTCAAACCT |

TABLE 1-continued

Primer Sequences for RT-PCR Amplification

| Target | SEQ ID No: | FWD Sequence (5'-3') | SEQ ID No: | REV Sequence (3'-5') |
|---|---|---|---|---|
| VWF | 5 | CCCTGGGTTACAAGGAAGAAAAT | 6 | AGTGTCATGATCTGTCCTCCTCTTAG |
| MMP1 | 7 | CGGTTTTTCAAAGGGAATAAGTACTG | 8 | GAAGCCAAAGGAGCTGTAGATGTC |
| MMP3 | 9 | TCCCAAGCAAATAGCTGAAGACT | 10 | TTCTTTGCATITGGGTCAAACTC |
| REN | 11 | GTGCACACTGGCCATCCA | 12 | AAACTCTGTGTAGAACTTTCGGATGA |
| SLC12A1 | 13 | ACTCCAGAGCTGCTAATCTCATTGT | 14 | AACTAGTAAGACAGGTGGGAGGTTCT |
| SLC22A6 | 15 | ACAATGATCC GCGCTGTCA | 16 | GTCGCGTCTG TTTCCCTTTC |
| SLC22A8 | 17 | TCTACACAAGTGAATTATACCCCACAGT | 18 | CGCGGGTCCACAGGTTACT |
| SLC22A12 | 19 | GGACCTGTATCTCCACGTTG TG | 20 | GATGTCCACGACACCAATGA AC |
| UMOD | 21 | CCTGAACTTGGGTCCCATCA | 22 | GCCCCAAGCTGCTAAAAGC |
| SPP1 | 23 | AGCCAATGATGAGAGCAATGAG | 24 | TGGAATTCACGGCTGACTTTG |
| ALB | 25 | TGCAAGGCTGACGATAAGGA | 26 | GTAGGCTGAGATGCTTTTAAATGTGA |
| PDCN | 27 | AGGATGGCAGCTGAGATTCTGT | 28 | AGAGACTGAAGGGTGTGGAGGTAT |
| NPHN | 29 | CTTCCCTGGGCACTTGTATG A | 30 | TCATAGATTCCTCTTGGATCCTGAT |
| CUBN | 31 | CCGGCTATCCAGGCACATA | 32 | CCTTCCAGCAGGAGCAACAA |
| LRP2 | 33 | GCACAGATGGAGAACGAGCAA | 34 | AGCAGGGAGCGAAGGTGAT |
| AQP9 | 35 | AAACAACTTCTGGTGGATTCCTGTA | 36 | GCTCTGGATGGTGGATTTCAA |

After the completion of the PCR reaction, the mRNA (as represented by the amount of PCR-amplified cDNA detected) for one or more markers is quantified. In certain embodiments, quantification is calculated by comparing the amount of mRNA encoding a disease marker to a reference value. In some embodiments the reference value will be the amount of mRNA found in healthy non-diseased patients. In other embodiments, the reference value is the expression level of a house-keeping gene. In certain such embodiments, beta-actin, or other appropriate housekeeping gene is used as the reference value. Numerous other house-keeping genes that are well known in the art may also be used as a reference value. In other embodiments, a house keeping gene is used as a correction factor, such that the ultimate comparison is the expression level of marker from a diseased patient as compared to the same marker from a non-diseased (control) sample. In several embodiments, the house keeping gene is a tissue specific gene or marker, such as those discussed above. In still other embodiments, the reference value is zero, such that the quantification of the markers is represented by an absolute number. In several embodiments a ratio comparing the expression of one or more markers from a diseased patient to one or more other markers from a non-diseased person is made.

In several other embodiments, kidney marker expression is measured before and/or after administration of a drug to a patient. In such embodiments, the expression profiles may be used to predict the efficacy of a drug compound (e.g. in treating kidney disease) or to monitor side effects of the drug compound (e.g., impact on kidney function). In some embodiments the drug monitored may have been administered to treat one or more of chronic kidney disease, acute renal failure, diabetic nephropathy, glomerulonephritis, glomerulosclerosis, focal segmental glomerulosclerosis, membranous nephropathy, minimal change disease, atherosclerosis, hypertension, cardiovascular diseases, obesity, hypercholesterolemia, diabetes, collagen diseases, cancer drug, infections, and/or immunosuppressive diseases. In some embodiments, a drug compound will induce the expression of a distinctive mRNA profile. Likewise, in other embodiments, a drug may inhibit one or more markers. In some such embodiments, the efficacy of drug treatment can be monitored by the disappearance of markers associated with a particular disease state.

In several embodiments, the analyses described herein are applicable to human patients, while in some embodiments, the methods are applicable to animals (e.g., veterinary diagnoses).

EXAMPLES

Specific embodiments will be described with reference to the following examples which should be regarded in an illustrative rather than a restrictive sense.

Example 1

Characterization of Kidney Function Through Analysis of Urine RNA-Associated Vesicles Given ready access to potentially large quantities of patient urine samples, use of urine as a diagnostic sample is common. Most current diagnostic tests measure solutes excreted in urine, or measure urine production rate, in order to characterize kidney function, or loss thereof due to damage or disease. However, the existence of vesicles present in the urine which are associated with RNA species is utilizes here to make a sensitive and specific diagnostic analysis of kidney function based on isolation and amplification of kidney specific markers.

Methods

Human urine samples (triplicate) from 3 healthy donors were applied to the filter membranes of a vesicle capturing filterplate (as described above) with vacuum, followed by centrifugation at 2000×g for 5 min. After centrifugation, 50 µL of Lysis Buffer was added to each well which were then incubated at 37° C. for 10 minutes to lyse the vesicles. The Lysis buffer was supplemented with 5 nM of reverse primers and/or antisense primers of target genes. Primer Sequences are shown in Table 1. The Lysis buffer was also optionally supplemented with synthetic RNA which served as a control. The filterplate was then placed onto a 96-well oligo(dT)-immobilized plate (GENEPLATE®) and centrifuged at 2,000×g for 5 minutes to transfer vesicle lysate to the GENEPLATE®). After centrifugation, the GENEPLATE®) was placed in a refrigerator overnight for the hybridization between oligo(dT) and polyA-tails of mRNA. The GENEPLATE®) was then washed 6 times with 150 µL of Wash Buffer (0.5 M NaCl, 10 mM Tris (pH 7.4), 1 mM EDTA). The cDNA was synthesized at 37° C. for 2 hours by addition to each well of 30 µL of reverse transcription buffer (50 mM KCl, 10 mM Tris-HCl (pH 8.3), 5.5 mM $MgCl_2$, 0.1% Tween 20) supplemented with 1.25 mM of each deoxynucleoside triphosphate, 4 units of rRNasin, and 80 U of MMLV reverse transcriptase.

The cDNA solution was then used for real time PCR using iTaq SYBR (BioRad, Hercules, Calif.). An aliquot of cDNA was mixed with an equal volume of 2× reaction mix containing 0.4 mM each of dATP, dCTP, dGTP, and dTTP, 50 U/ml iTaq DNA polymerase, 6 mM Mg2+, SYBR Green I, ROX reference dye, stabilizers. This mixture was supplemented with forward and reverse gene specific primers. The cycle threshold (Ct), at which fluorescence exceeded background levels, was determined by analysis with SDS software (Applied Biosystems). The Ct value was used to calculate the original relative amount of the marker mRNA.

Results

Figure 1A:
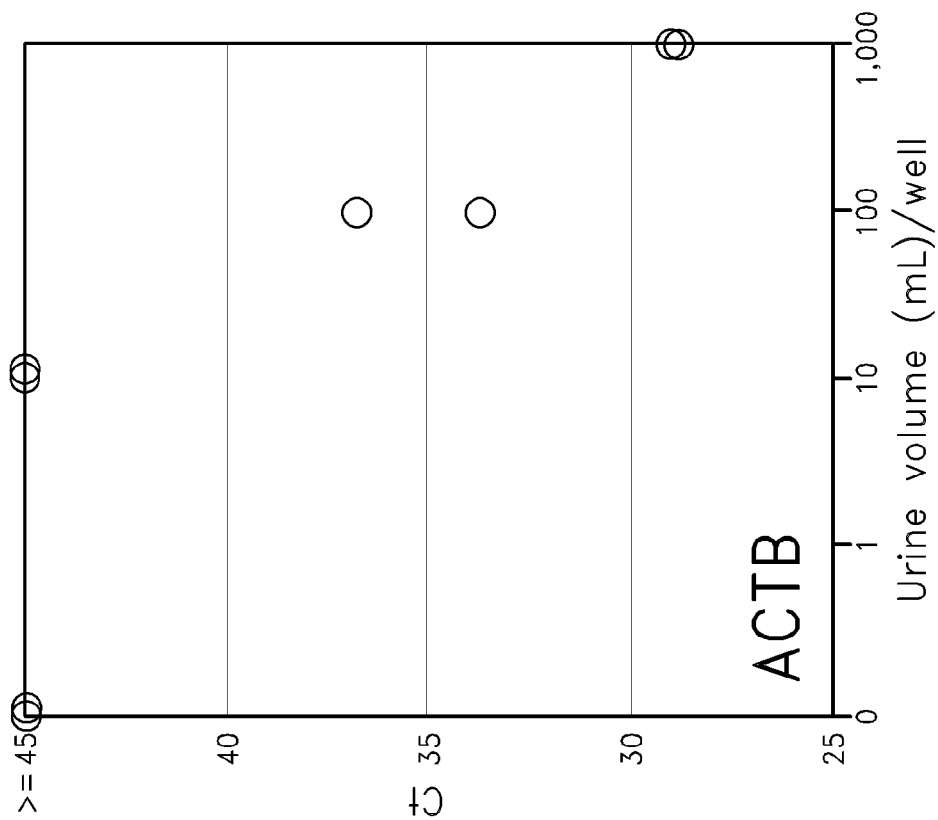

As shown in FIG. 1A, control gene (β-actin, ACTB) and FIG. 1B kidney specific gene (solute carrier family 12A1 (SLC12A1, sodium potassium chloride transporter) were detected from 100 µL of whole urine in a dose dependent manner. The delta Ct between 100 and 1000 µL (10 folds) was approximately 3 ($2^3$=8 folds), which is within a theoretical value. These results demonstrate that usable RNA can be obtained from urine vesicles by embodiments of the methods described herein. When crude whole urine was used, maximal urine volume applicable to each filterplate well was approximately 1 mL due to the presence of cell debris. However, when urine sample was centrifuged at 2000×g for 15 min prior to addition to the filterplate (to pellet cellular debris), more than 20 mL supernatant was applicable to filterplate (data not shown). Thus several embodiments are particularly useful for urine, because large a volume of urine is easily obtainable and processable.

Figure 2B:
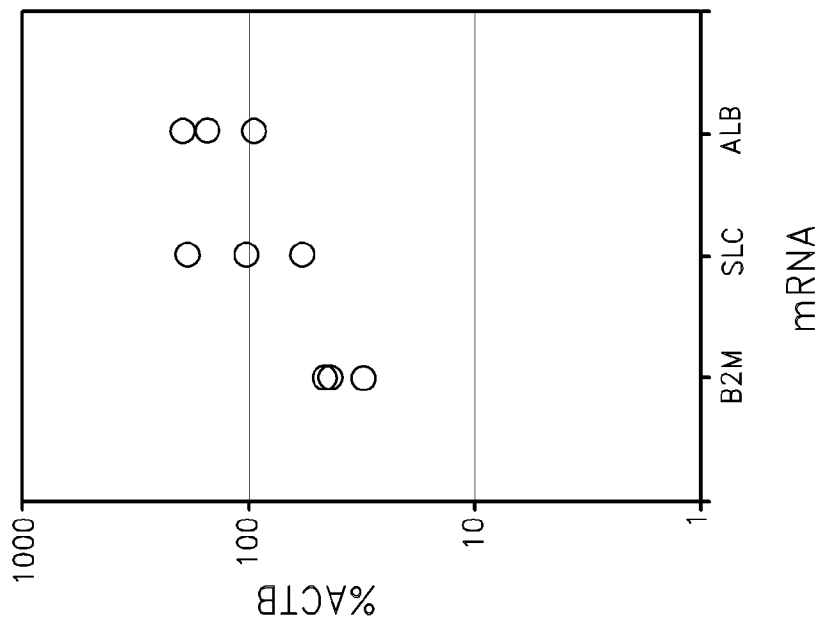
FIGS. 2A-2B depicts RT-PCR results from 3 donors' urine samples.
Figure 2A:
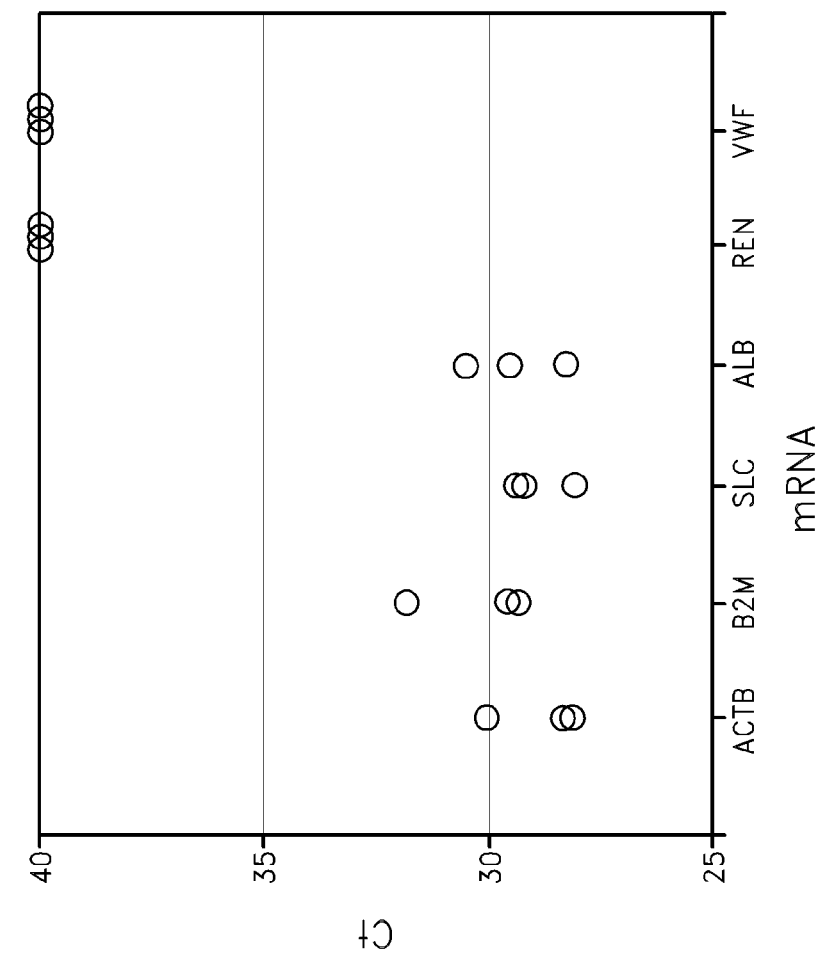

Using these methods, therefore, additional kidney markers were analyzed. One mL of patient urine was applied to the filter well in triplicate and analyzed as described above using gene-specific primers. Delta Ct data is shown in FIG. 2A while 2B shows the same data after normalization to % ACTB. Each symbol represents the mean value of triplicate samples in each donor. As shown in FIG. 2A, two control genes (ACTB and β2 microglobulin (B2M)) as well as kidney-specific SLC12A1, and albumin (ALB, liver-specific, but also expressed in kidney) were quantified in a similar degree. Renin (REN), another kidney-specific gene, and Von Willebrand factor (VWF) an endothelial cell marker, were not detected. These results were also normalized by the values of ACTB (FIG. 2B).

Figure 3C:
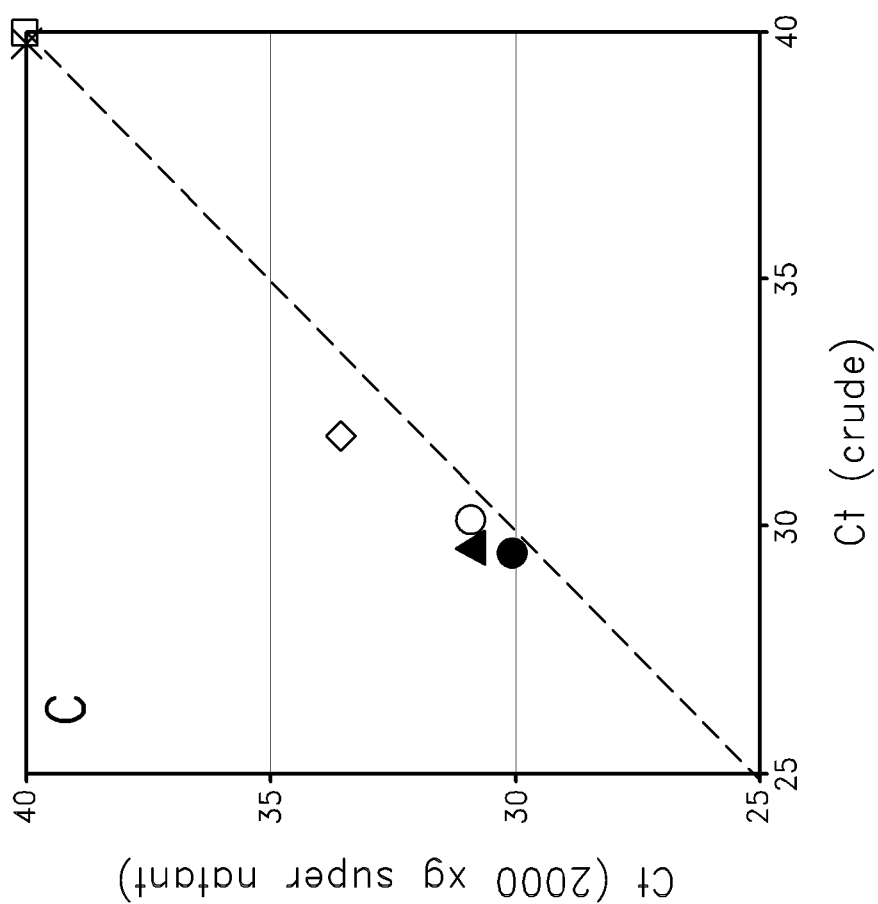

To determine the effect of freezing and thawing of urine samples on the quality of RNA isolated from urine vesicles, non-frozen urine was compared to urine that had undergone a complete freeze-thaw cycle. One mL of each type of urine was analyzed in triplicate as described above. As shown in FIG. 3A, the PCR results of frozen samples were similar to those of non-frozen fresh urine samples. Moreover, the number of freeze-thaw cycles did not affect mRNA analysis (FIG. 3B). Crude urine was also compared to urine that had be centrifuge to remove the cellar fraction. Although the amounts of mRNA in 2,000×g supernatant of urine were slightly lower than those of crude urine (FIG. 3C), mRNAs were clearly detected in the non-cellular faction of urine, thereby demonstrating that vesicles isolated from the non-cellular fraction of urine can be used for RNA analysis.

Figure 4A:
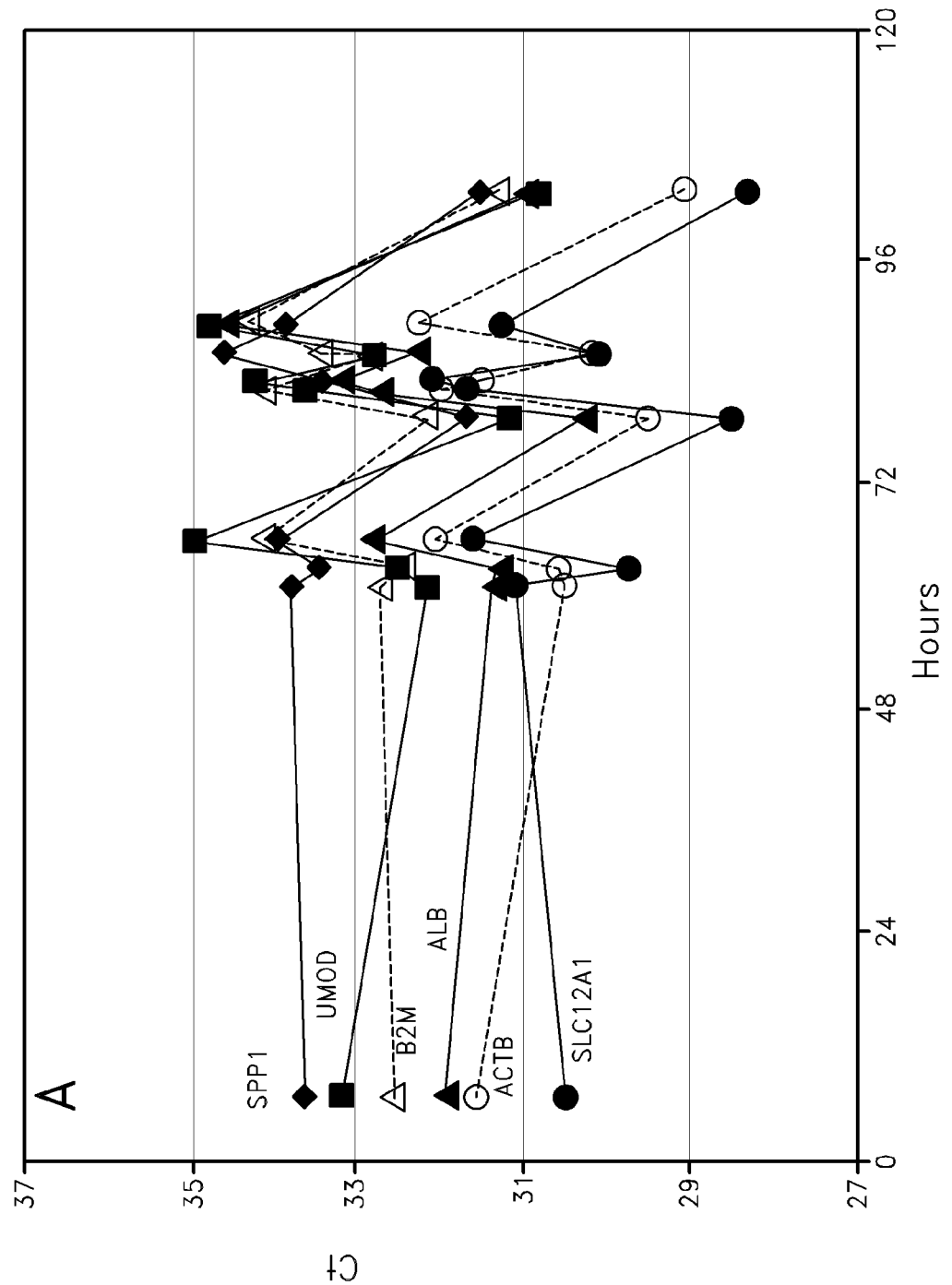
FIGS. 4A-4B depicts monitoring of urine mRNAs over time.
Figure 4B:
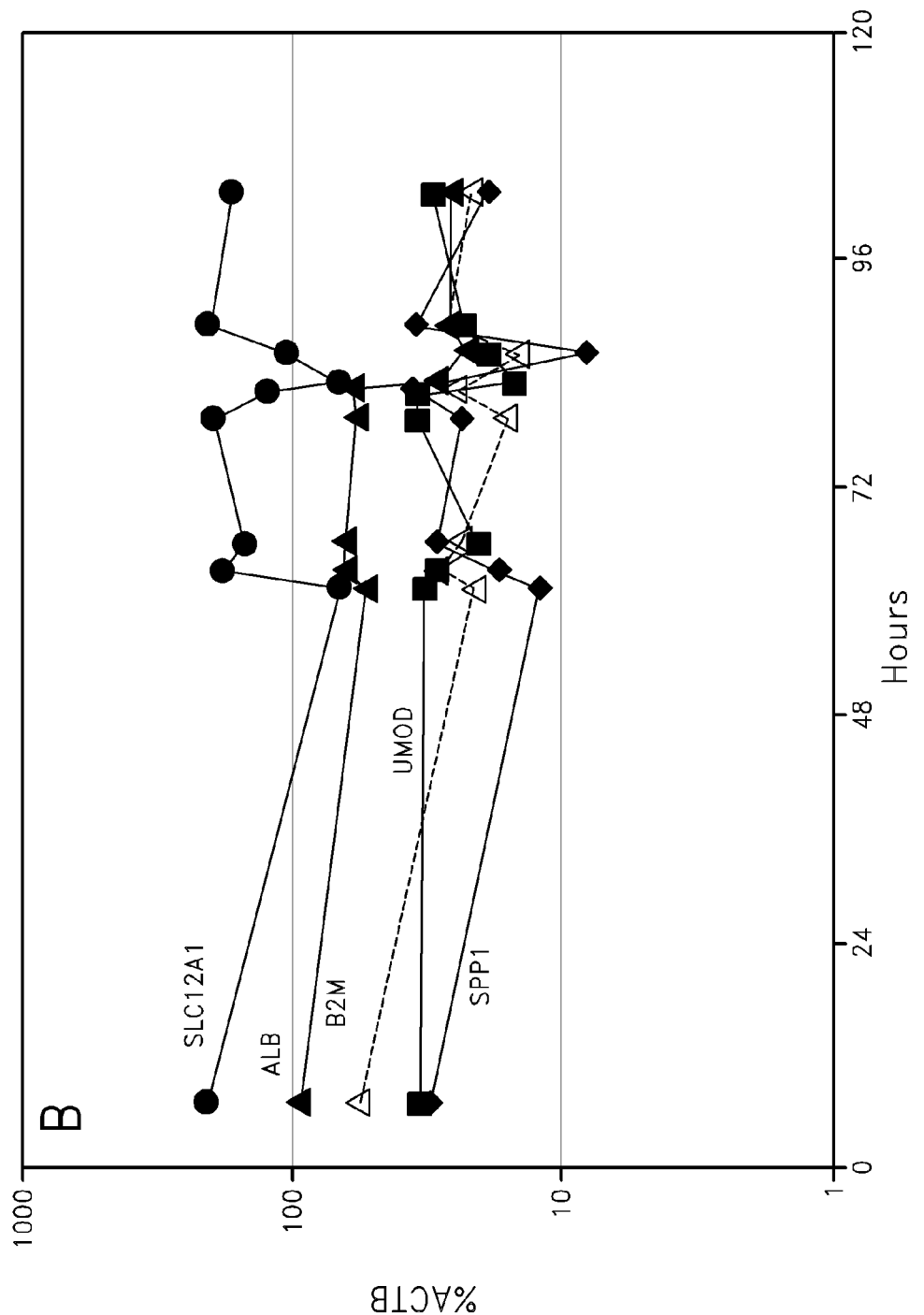
Figure 5A:
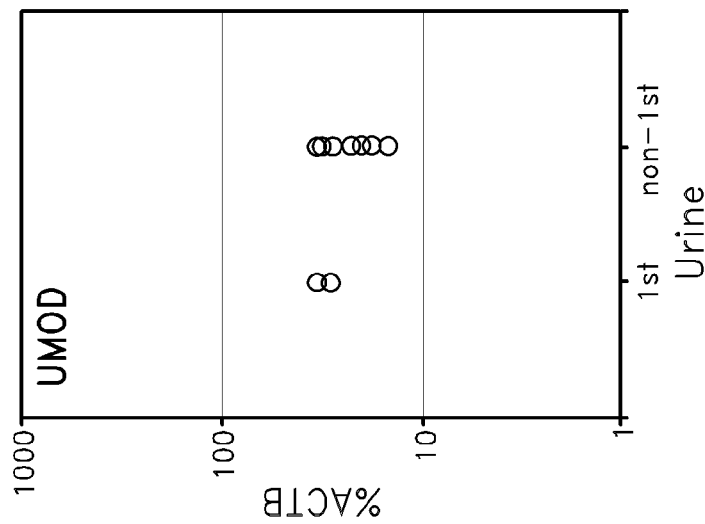
FIGS. 5A-5F depicts a comparison of a morning urine sample as compared to pooled urine from subsequent samples.
Figure 5B:
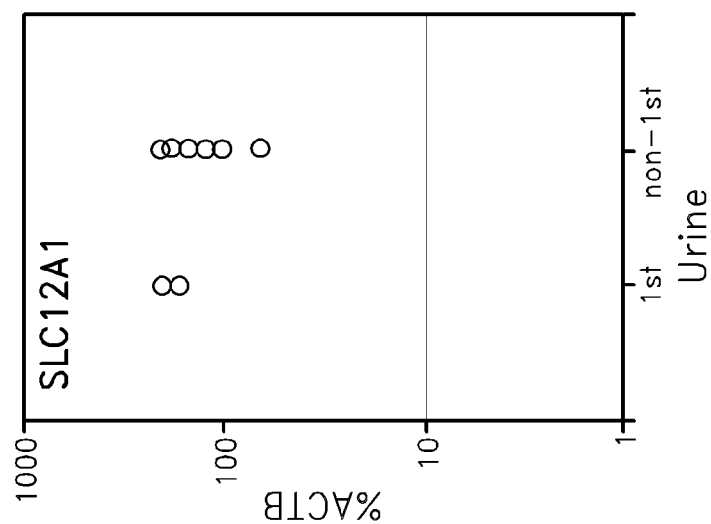
Figure 5C:
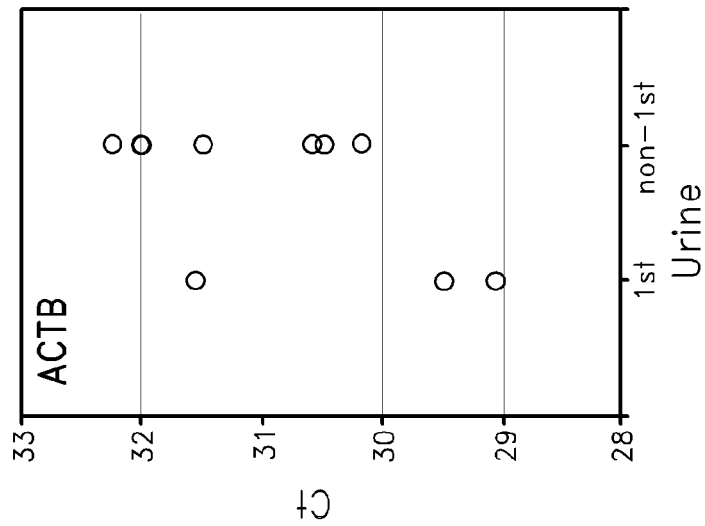
Figure 5F:
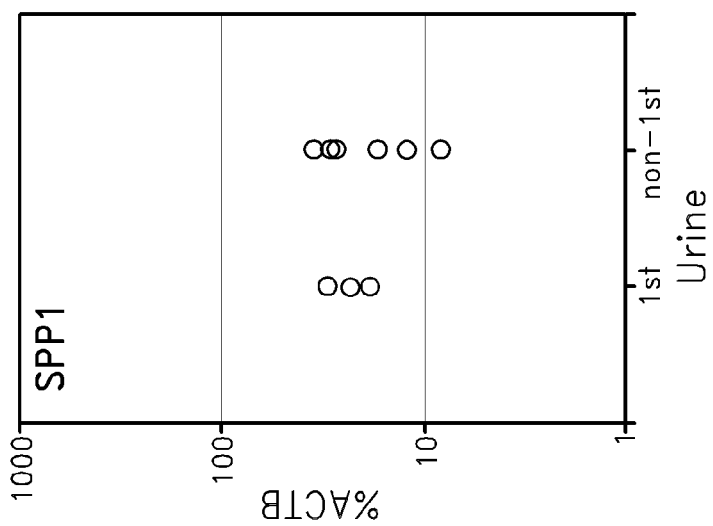
Figure 5E:
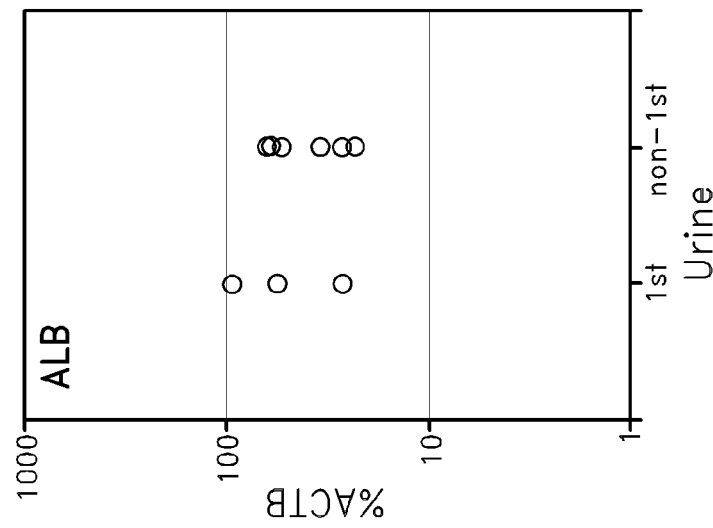
Figure 5D:
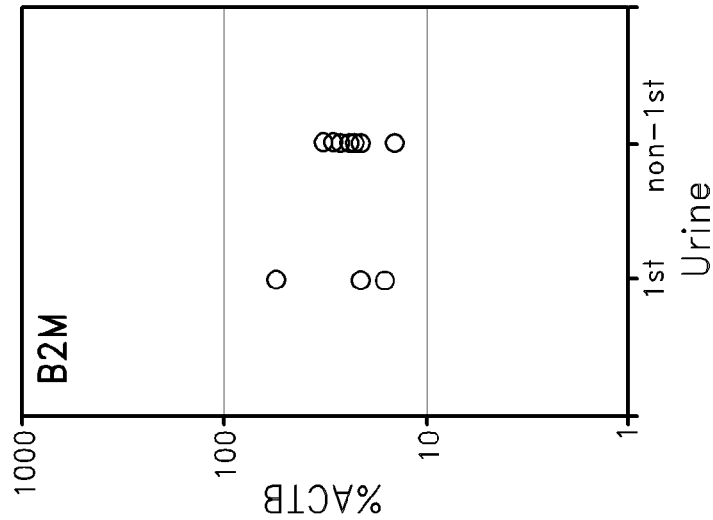

In order to demonstrate the ability of accurately monitor a patient over time, the daily fluctuation of urine mRNAs was analyzed using urine samples collected from a single donor over a 5 day period. Collected samples were immediately stored at −80° C. Samples were later thawed and centrifuged. Five mL of 2000×G supernatant of thawed urine was applied to the filterplate in triplicate, and 2 control genes (ACTB, B2M) and 4 kidney specific genes (SLC12A1, ALB, UMOD, and SPP1) were quantified. FIG. 4A shows delta Ct data, while FIG. 4B shows Ct values transformed to % ACTB.

SLC12A1, ALB, UMOD, SPP1 as well as ACTB and B2M mRNAs were constantly detected from all urine samples (FIG. 4A), while other genes were not detected. While SLC12A1, ALB, UMOD, SPP1 are used in some embodiments, in other embodiments, depending on the individual and the state of the kidney, other markers are used. The time-course data appear to indicate that there were daily fluctuations in kidney-specific marker expression, perhaps reflecting a circadian-esque alteration in kidney function.

As shown in FIGS. 5A-5F, there did not appear to be a defined change in kidney marker expression over time. FIGS. 5A-5F depicts kidney specific marker expression in a single morning urine sample as compared to pooled urine from subsequent samples. While statistical significance was not seen, in some embodiments, depending on the individual and the marker being evaluated, changes in gene expression over time may be detected.

Discussion

The data presented above demonstrate that RNA can be isolated, processed and successfully evaluated for gene expression when isolated from vesicles that are present in patient urine samples. In order to characterize the tissue expression profiles of markers used in this experiment, tissue-specific (body-wide) expression data was summarized in Table 2.

TABLE 2

Expression profile of various genes used in this study

| | ACTB | B2M | VWF | MMP1 | MMP3 | REN | SLC12A1 | SLC22A6 | SLC22A8 | SLC22A12 | UMOD | SPP1 | ALB |
|---|---|---|---|---|---|---|---|---|---|---|---|---|---|
| adipose tissue | 4,484 | 3,040 | 836 | 0 | 0 | 0 | 0 | 0 | 0 | 0 | 0 | 152 | 0 |
| adrenal gland | 4,018 | 3,328 | 59 | 0 | 0 | 0 | 0 | 0 | 0 | 0 | 0 | 179 | 29 |
| ascites | 6,615 | 1,997 | 0 | 0 | 0 | 0 | 0 | 0 | 0 | 0 | 0 | 0 | 24 |
| bladder | 3,783 | 862 | 0 | 33 | 0 | 33 | 0 | 0 | 0 | 0 | 33 | 199 | 1,626 |
| blood | 7,283 | 5,132 | 8 | 56 | 0 | 0 | 0 | 0 | 0 | 0 | 0 | 298 | 2,118 |
| bone | 2,757 | 1,573 | 55 | 41 | 139 | 0 | 0 | 0 | 0 | 0 | 0 | 515 | 0 |
| bone marrow | 3,990 | 3,501 | 0 | 0 | 0 | 0 | 0 | 0 | 0 | 0 | 0 | 223 | 0 |
| brain | 4,004 | 207 | 57 | 1 | 2 | 0 | 10 | 14 | 15 | 0 | 20 | 642 | 66 |
| cervix | 6,433 | 701 | 0 | 0 | 0 | 0 | 0 | 0 | 0 | 0 | 0 | 41 | 0 |
| connective tissue | 4,278 | 902 | 100 | 4,646 | 9,934 | 0 | 13 | 0 | 0 | 0 | 0 | 53 | 73 |
| ear | 1,896 | 61 | 0 | 0 | 0 | 0 | 0 | 0 | 0 | 0 | 0 | 1,774 | 0 |
| embryonic tissue | 4,864 | 120 | 0 | 41 | 0 | 4 | 0 | 0 | 0 | 0 | 0 | 403 | 268 |
| esophagus | 13,655 | 1,286 | 49 | 2,275 | 197 | 0 | 0 | 0 | 0 | 0 | 0 | 49 | 0 |
| eye | 2,269 | 368 | 94 | 4 | 33 | 0 | 0 | 9 | 52 | 0 | 0 | 278 | 18 |
| heart | 2,325 | 509 | 188 | 0 | 0 | 0 | 0 | 0 | 0 | 0 | 11 | 66 | 13,044 |
| intestine | 4,806 | 967 | 76 | 63 | 25 | 76 | 0 | 0 | 0 | 0 | 0 | 38 | 8 |
| kidney | 3,076 | 446 | 56 | 9 | 0 | 37 | 752 | 404 | 465 | 583 | 10,956 | 1,735 | 1,213 |
| larynx | 4,084 | 530 | 81 | 163 | 122 | 0 | 0 | 0 | 0 | 0 | 0 | 449 | 0 |
| liver | 2,466 | 1,319 | 9 | 4 | 0 | 0 | 4 | 0 | 0 | 0 | 0 | 187 | 58,985 |
| lung | 3,696 | 1,652 | 124 | 277 | 20 | 2 | 0 | 0 | 0 | 0 | 0 | 233 | 221 |
| lymph | 8,603 | 472 | 0 | 0 | 0 | 0 | 0 | 0 | 0 | 0 | 0 | 0 | 22 |
| lymph node | 3,144 | 1,664 | 0 | 0 | 0 | 0 | 0 | 0 | 0 | 0 | 0 | 10 | 10 |
| mammary gland | 3,177 | 478 | 116 | 0 | 0 | 0 | 0 | 0 | 0 | 0 | 0 | 90 | 9,552 |
| mouth | 565 | 1,071 | 59 | 0 | 0 | 0 | 0 | 0 | 0 | 0 | 0 | 59 | 0 |
| muscle | 804 | 425 | 73 | 46 | 18 | 0 | 27 | 9 | 0 | 0 | 9 | 36 | 942 |
| nerve | 2,338 | 884 | 442 | 0 | 0 | 0 | 0 | 0 | 0 | 0 | 0 | 189 | 0 |
| ovary | 3,741 | 662 | 68 | 19 | 0 | 19 | 0 | 0 | 0 | 0 | 0 | 107 | 0 |
| pancreas | 2,466 | 2,489 | 23 | 41 | 0 | 4 | 0 | 0 | 0 | 0 | 0 | 589 | 41 |
| parathyroid | 290 | 2,324 | 0 | 0 | 0 | 0 | 0 | 0 | 0 | 0 | 0 | 0 | 145 |
| pharynx | 1,614 | 23,102 | 144 | 0 | 0 | 0 | 0 | 0 | 0 | 0 | 0 | 120 | 0 |
| pituitary gland | 896 | 2,749 | 0 | 0 | 0 | 0 | 0 | 0 | 0 | 0 | 0 | 0 | 0 |
| placenta | 2,702 | 833 | 221 | 95 | 3 | 10 | 0 | 0 | 0 | 0 | 0 | 1,069 | 52 |
| prostate | 2,428 | 902 | 52 | 0 | 5 | 0 | 0 | 0 | 0 | 0 | 5 | 15 | 0 |
| salivary gland | 6,067 | 345 | 0 | 0 | 0 | 0 | 0 | 0 | 0 | 0 | 0 | 0 | 0 |
| skin | 4,389 | 529 | 9 | 581 | 61 | 4 | 0 | 0 | 0 | 0 | 0 | 122 | 0 |
| spleen | 6,346 | 2,664 | 388 | 0 | 0 | 0 | 0 | 0 | 0 | 0 | 0 | 18 | 7,660 |
| stomach | 6,297 | 2,222 | 92 | 113 | 72 | 0 | 0 | 0 | 0 | 0 | 0 | 92 | 10 |
| testis | 2,326 | 87 | 36 | 0 | 3 | 3 | 0 | 0 | 0 | 0 | 0 | 66 | 9 |
| thymus | 4,582 | 1,478 | 36 | 0 | 0 | 0 | 0 | 0 | 0 | 0 | 0 | 12 | 184 |
| thyroid | 6,027 | 729 | 208 | 7,799 | 62 | 0 | 0 | 0 | 0 | 0 | 0 | 20 | 0 |
| tonsil | 12,146 | 1,232 | 0 | 0 | 0 | 0 | 0 | 0 | 0 | 0 | 0 | 0 | 0 |
| trachea | 724 | 476 | 133 | 0 | 0 | 0 | 0 | 0 | 0 | 0 | 0 | 57 | 0 |
| umbillical cord | 15,696 | 1,017 | 3,996 | 3,996 | 0 | 0 | 0 | 0 | 0 | 0 | 0 | 145 | 0 |
| uterus | 5,825 | 1,495 | 98 | 42 | 4 | 0 | 0 | 0 | 0 | 0 | 0 | 145 | 12 |
| vascular | 5,178 | 1,982 | 288 | 33,575 | 0 | 0 | 0 | 0 | 0 | 0 | 0 | 38 | 0 |

Each value represents the frequency of expression in 1,000,000 cDNA clones.
Data were derived from EST (expression sequence tag) database in UniGene.

As shown in Table 2, ACTB and B2M were found in all tissues, confirming that these genes worked as housekeeping control genes. Other embodiments use other housekeeping genes, however. As discussed above, vWF, MMP1, and MMP3 were not detected in urine samples from these patients. However, these results are explained in part by the low expression level of these mRNAs in kidney (Table 2). However, in other patients or in certain disease/damage states, vWF is detected, which may indicate some endothelial damage in the kidneys. Similarly, in some embodiments, MMP1 and/or MMP3 is detected in urine, which may indicate fibrotic changes in the kidney, as both of these MMPs are highly expressed in connective tissue (Table 2). Among the kidney-specific genes evaluated (REN, SLC12A1, SLC22A6, SLC22A8, SLC22A12, UMOD), SLC12A1 was abundantly expressed in urine more than ACTB and UMOD (FIG. 2, 4, 5). These data suggest that, in some embodiments SLC12A1 is a highly sensitive marker of kidney function. SLC12A1 is found on the apical membrane of the thick ascending limb of Henle's loop and the macula densa of the kidney. It accounts for a large degree of the sodium chloride resorption in the thick ascending limb. Moreover, it is sensitive to certain diuretics, such as furosemide and bumetanide, drugs that may be used in treating hypertension. Thus, in several embodiments, detection changes in expression of SLC12A1 may be indicative of altered salt balance, change in function of or damage to the kidney due to anti-hypertensive therapy, etc. In several embodiments, this is particularly advantageous, as changes in SLC12A1 may help identify an individual patient's sensitivities to certain therapies long before recognizable symptoms are presented. Thus in several embodiments, the variation in SLC12A1 expression are varied (and can be correlated to) certain kidney diseases, stages of disease, and or responsiveness to therapies.

In other embodiments, other kidney markers are used in a similar manner, depending on the therapeutic agent being administered or the disease being treated. For example, SLC22A6 is sodium-dependent, and SLC22A8 is sodiumindependent transporter and excretor of organic anions, while SLC22A12 is urate-anion exchanger that functions to regulate the level of urate in the blood. Given the varied mechanism of transport (as compared to SLC12A1), detection of these SLC22As in urine, in some embodiments, may indicate other molecular pathological changes in kidney. Moreover, UMOD is the most abundant protein in normal urine. In several embodiments, changes in expression of UMOD are indicative of a departure from normal kidney function. As discussed above, the measurement of SLC12A1 and other genes in vesicles isolated from urine samples provides a rapid, accurate, and simple diagnostic test for assessment of kidney functions.

Example 2

Analysis of Urine RNA-Associated Vesicles to Determine Post-Transplant Kidney Function Urine samples were collected from 10 adult healthy donors (3 different samples from a single donor, for a total of 12 samples) and 68 post-kidney transplantation patients. Post-transplant patients were further categorized by the values of serum creatinine (28 patients were ≤1.2 mg/dl and 40 patients were >1.2 mg/dl). Serum creatinine is a commonly used measure of kidney function, as creatinine is a muscle-breakdown waste product that should be filtered (and removed from the bloodstream) by the kidney. Normal serum creatinine levels range from about 0.8 to about 1.2 mg/dl. Increased creatinine levels indicate a reduction in kidney function (e.g., reduced filtration efficiencies). Urine samples were processed as described above.

As shown in Table 3, more than 75% of all samples, regardless of their category (e.g., control, normal or high creatinine) detected ACTB. These data indicate the detectable presence of exosomes in urine of all the groups.

tioning as a linker between the plasma membrane and the cytoskeleton. Reductions in podocin (or mutations) lead to reduced glomerular filtration and may cause one or more of albuminuria, hypercholesterolemia, hypertension, and renal failure as in nephrotic syndrome.

Cubilin is involved in receptor-mediated tubular reabsorption of several important ligands from glomerular ultrafiltrate and is expressed in the proximal tubules of the kidney (along with megalin (also known as LRP2), another receptor). Proteins filtered in renal glomeruli are normally removed from the tubular fluid by cubulin/megalin-mediated endocytosis. After endocytic uptake, the proteins are transferred to lysosomes for degradation, while cubulin and megalin are returned to the tubular surface to continue reabsorption of various proteins. Normal urine has low protein concentration in humans. Cubilin and megalin not only facilitate removal of proteins from the kidney ultrafiltrate but also to conserve a variety of essential substances such as vitamins and trace elements carried by plasma proteins. Reduction of their expression under certain circumstances, such as diseases affecting the glomeruli, can overload the filtration/reabsorption system, resulting in proteinuria and/or increased plasma protein concentrations. Consistently high levels of plasma protein can further damage the glomeruli, potentiating the proteinuria, eventually leading to compromised kidney function.

Uromodulin is one of the most abundant proteins excreted normally in urine, however, mutations in uromodulin cause alterations in its solubility and resultant deposits in the kidney. These deposits progressively grow and eventually disrupt normal kidney function.

SLC12A1, as discussed above, is a solute carrier protein that is essential for the normal function of the kidney. It is involved in the regulation of ion flux into and out of kidney cells. It is a key player in the mechanism by which kidneys

TABLE 3

Detection of Kidney-specific mRNAs in Urine Exosome

|  |  | ACTB | PDCN | NPHN | CUBN | LRP2 | UMOD | SLC12A1 | ALB | AQP9 |
|---|---|---|---|---|---|---|---|---|---|---|
| Control (n = 12) | # positive | 12 | 7 | 0 | 10 | 8 | 12 | 12 | 12 | 10 |
|  | % | 100 | 58 | 0 | 83 | 67 | 92 | 100 | 100 | 83 |
| sCr = <1.2* (n = 28) | # positive | 21 | 6 | 0 | 9 | 4 | 13 | 12 | 18 | 7 |
|  | % | 75 | 21 | 0 | 32 | 14 | 46 | 43 | 64 | 25 |
|  | p (vs control)** | n.s. | p < 0.05 | n.s. | p < 0.01 | p < 0.001 | p < 0.01 | p < 0.001 | p < 0.05 | p < 0.001 |
| sCr >1.2* (n = 40) | # positive | 39 | 5 | 1 | 20 | 13 | 19 | 15 | 24 | 10 |
|  | % | 87 | 13 | 3 | 50 | 33 | 48 | 38 | 60 | 25 |
|  | p (vs control)** | n.s. | p < 0.001 | n.s. | p < 0.05 | p < 0.05 | p < 0.01 | p < 0.001 | p < 0.01 | p < 0.001 |
|  | p (vs sCr = 1.2)** | n.s. | n.s. | n.s. | n.s. | n.s. | n.s. | n.s. | n.s. | n.s. |

*Post-kidney transplantation patients with serum creatinin = <1.2 or >1.2 mg/dl.
**Chi square test The incidence of detection of podocin (PDCN), cubulin (CUBN), low density lipoprotein receptor related protein 2 (LRP2), uromodulin (UMOD), SLC12A1, albumin (ALB), and aquaporin 9 (AQP9) mRNA were all significantly lower in samples from post-transplant patients (regardless of serum creatinine levels) compared with that of control subjects. No significant differences were detected between the two groups of patients when separated based on serum creatinine levels.

Podocin is a protein which lines the podocytes of Bowman's capsule in the kidney. It assists in maintaining the barrier at the glomerular basement membrane and plays a role in the regulation of glomerular permeability, as well as funcreabsorb salt from the urine back into the bloodstream, which plays a role in the maintenance of body fluid levels (e.g., water volume) and blood pressure.

Albumin is a marker of proximal tubule function, as normally most proteins are retained by the kidneys. Release of albumin in small quantities into the urine (microalbuminuria) can be indicative of deteriorating kidney function. Microalbuminuria can also be an indicator for development of progressive kidney damage which leads to proteinuria. AQP9 is a marker of distal tubule function, an area of the kidney that functions primarily to concentrate the urine by reabsorbtion of water in the distal tubule.

Figures 6G, 6H:
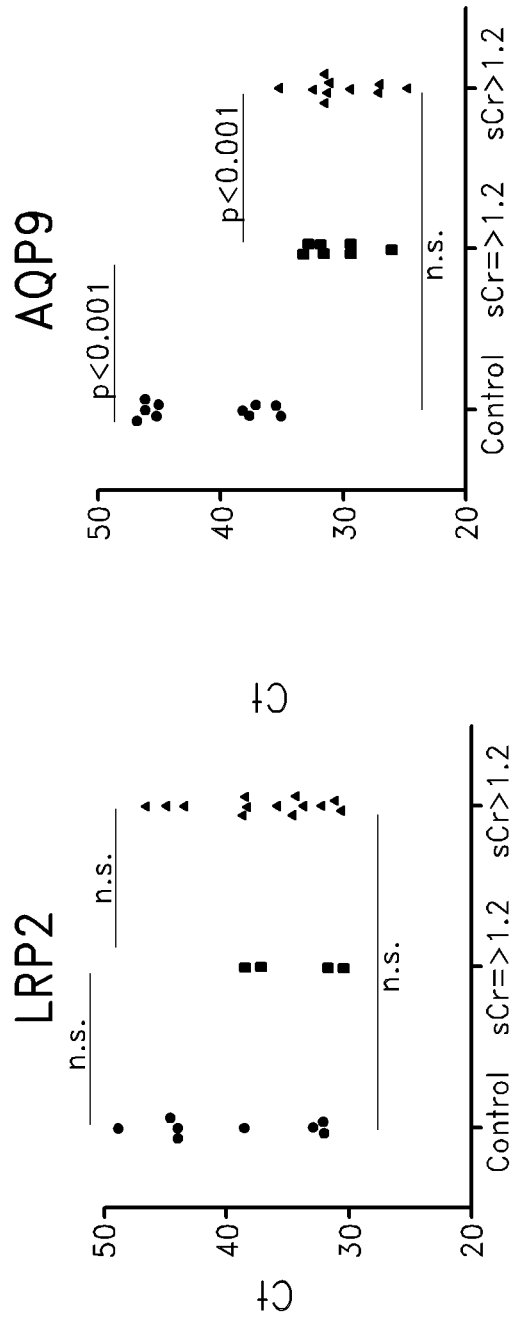

In order to further evaluate the expression data of Table 3, the expression levels of the positively detected mRNA among the three groups were compared. While beta-actin was detected in more than 75% of the total subjects, beta-actin levels were significantly higher in the control group as compared with the two patient groups (see FIG. 6A). This data indicates that, despite one patient group having normal serum creatinine levels, the amount of exosomes present in their urine is less than that of control patients (and not significantly different from patients with clinically elevated serum creatinine. Unlike beta-actin, the levels of PDCN, CUBN, UMOD, SLC12A1, LRP2 were no longer calculated to be different among 3 groups, thereby suggesting that the normalization with respect beta-actin introduced experimental error and possible false negative results. Interestingly, despite normalization to beta-actin, expression levels of ALB (marker of proximal tubule function) was significantly lower in the patient ($p<0.001$ versus control), whereas the levels of AQP9 (marker of distal tubule function) were significantly higher in the patient groups (($p<0.001$ versus control). This suggests that the actual differences between control and patient albumin and/or aquaporin were large enough to remain significant despite the beta-actin-induced blunting of the statistical analysis. Moreover, significant differences were found between the control group and the normal serum creatinine patient group, which suggests that several embodiments of the methods disclosed herein for exosome mRNA analysis are more sensitive than conventional serum creatinine analysis.

Figures 7A, 7B:
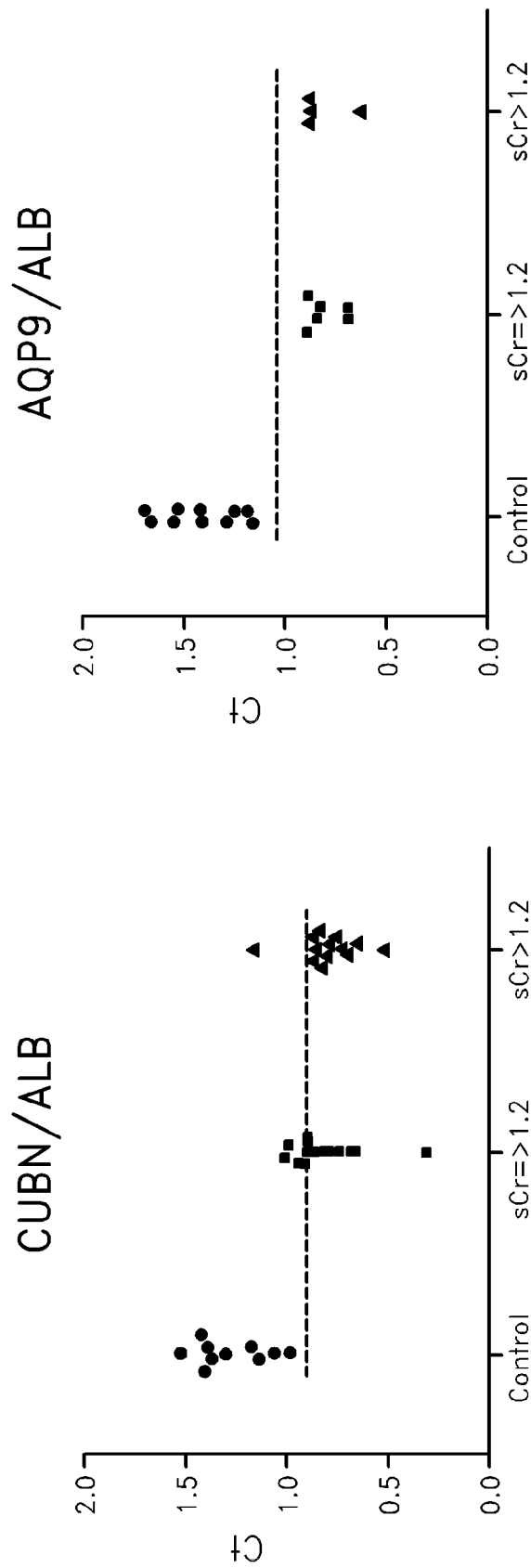
FIGS. 7A-7F depict alternative normalization schemes for data analysis.
Figures 7C, 7D:
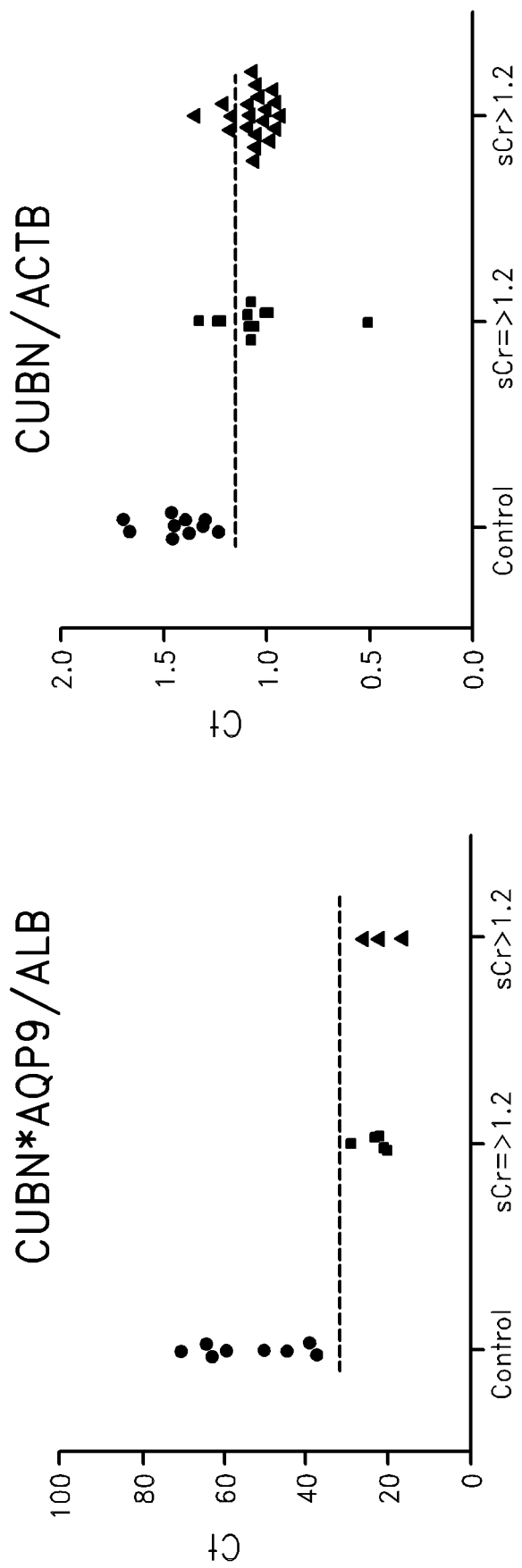
Figure 7F:
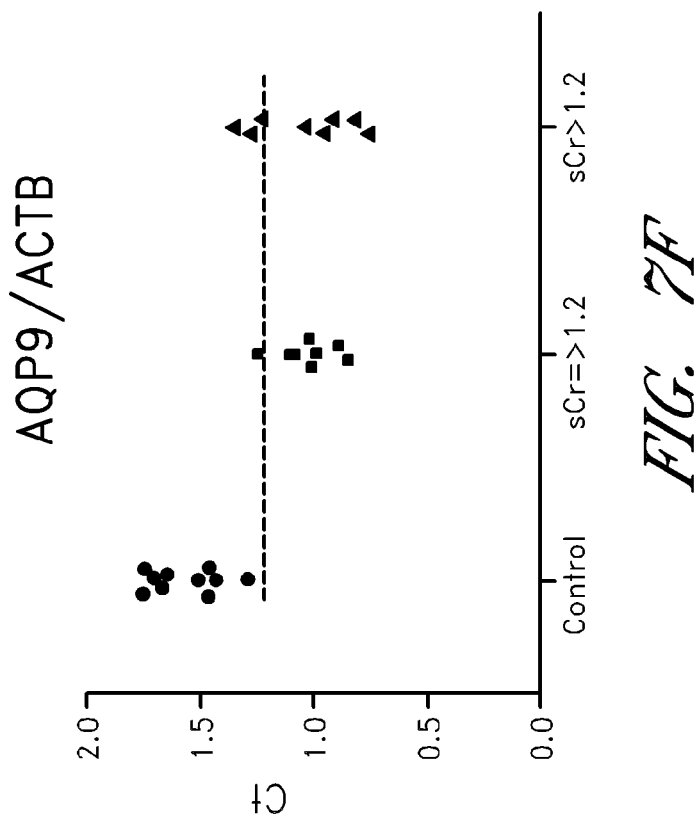
Figure 7E:
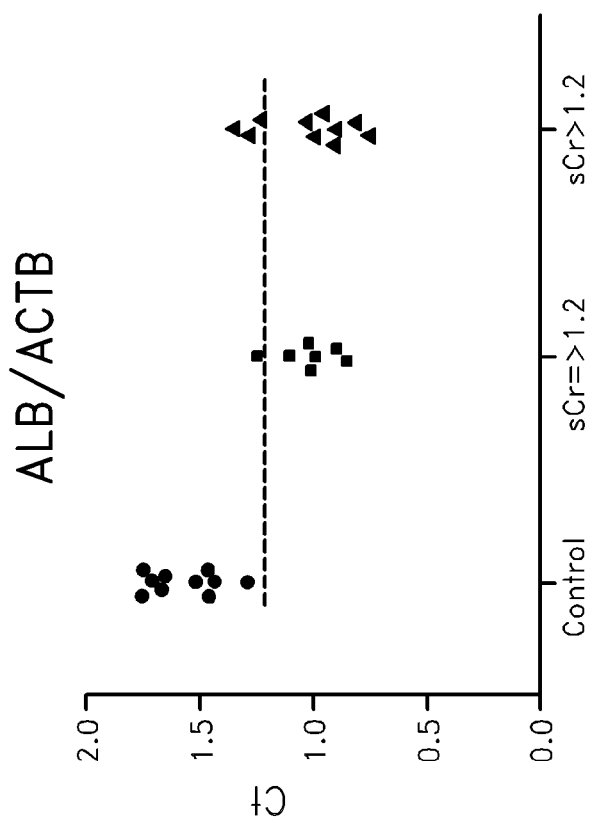

Due to the varying concentrations of exosomes in urine samples from various subjects (and even within an individual subject's individual samples), normalization to albumin levels was performed (based on its opposite pattern of expression as compared to beta-actin, as shown in FIG. 6). In FIGS. 7A-7C, CUBN, AQP9, and CUBNxAQP9 data are shown normalized with respect to ALB. As a result, AQP9/ALB and CUBNxAQP9/ALB (7B and 7C, respectively) separated control and patients groups without any overlap. The overlap was not eliminated by the normalization with ACTB (FIGS. 7D-7F).

These data also indicate that several of the markers tested are suitable for characterizing kidney function, and therefore in identifying early disease states. While albumin is consistently detected in control subjects, it is often undetectable in post-transplant patients, and when detected, albumin levels are significantly reduced in post-transplant patients. Because albumin is associated with proximal tubule function, the significant difference in albumin expression between normal and post-transplant subject suggests that albumin expression levels can be used to characterize kidney function. Thus, in several embodiments, albumin is used as a highly sensitive marker of kidney function. For example, the reduced albumin levels in post-transplant patients may suggest compromised tubule structure or hyperactivity, either of which could result in excessive removal of albumin from the urine exosomes.

Additionally, aquaporin 9 expression is significantly different between normal and post-transplant patients. In contrast to albumin, the levels of AQP9 were significantly higher in patients as compared to control individuals (FIGS. 6H and 7B), despite the overall lower percent detection of aquaporin in patient urine exosomes (Table 3). Additionally, other markers (or combinations of markers) are used in some embodiments to determine kidney function. For example, cubulin expression levels (FIG. 7A) indicate a trend towards reduced expression in the urine exosomes of post-transplant patients. In several embodiments, multiplex analysis is performed, for example, a combination of markers is used to assess kidney function. For example (see FIG. 7C), simultaneous evaluation of cubulin and aquaporin expression is shown. In some embodiments, evaluation of multiple markers can provide a more precise and/or more sensitive diagnosis. Tissue specific markers may be evaluated in conjunction with disease specific markers such that one marker is used to identify a specific disease and the other marker is used to identify the specific tissue type affected. In some embodiments, the use of multiple markers can also lead to tailored therapies. For example, if a first marker is specific to the proximal tubule function of the kidney and a second marker is specific to the distal tubule, detection of significant changes of both in a multiplex analysis may be suggestive of damage to the tubule (or the kidney) as a whole. In contrast, changes in expression in one or the other marker may suggest site-specific damage or injury that compromise kidney function in a more localized area. In still additional embodiments, use of three or more markers is used to provide a more detailed analysis of kidney function. Importantly, exosome analysis as disclosed herein allows impairment of kidney function to be detected even when conventional tests (serum creatinine) is normal. As a result, the methods disclosed herein can lead to earlier diagnosis and early treatment, which may help reduce negative effects on kidney function.

Various embodiments of the present invention have been described above. Although this invention has been described with reference to these specific embodiments, the descriptions are intended to be illustrative of the invention and are not intended to be limiting. Various modifications and applications may occur to those skilled in the art without departing from the true spirit and scope of the invention as defined in the appended claims.

What is claimed is:

1. A method for administering a therapy to a subject based on the kidney function of the patient, the method comprising:
   (A) having a first sample of urine from a patient sent to a laboratory, wherein the sample comprises vesicles comprising RNA, for the labatory to an assay comprising the following steps:
      (1) capturing the vesicles from the first urine sample, wherein the capturing comprises:
         (a) loading at least a portion of the first sample of biological fluid into a sample loading region of a vesicle capture device;
         (b) passing the sample from the sample loading region through a vesicle-capture material in the vesicle capture device, the vesicle-capture material comprising a plurality of layers of glass-like materials, thereby producing a supernatant,
      wherein the plurality of layers of glass like materials comprises at least a first layer and a second layer of glassfiber, and
      wherein the first layer of glassfiber is configured to capture material from the sample that is about 1.6 microns or greater in diameter, and wherein the second layer of glassfiber is configured to capture vesicles having a minimum size from about 0.6 microns to about 0.8 microns in diameter, and having a maximum size of less than 1.6 microns; and
         (c) passing the supernatant receiving region of the vesicle capture device, wherein the passings result in capture of the vesicles from the sample on or in the vesicle-capture material, thereby capturing the vesicles;

(2) lysing the captured vesicles to release the RNA, wherein the RNA comprises one or more RNA selected from the group consisting of UMOD, vWF, MMP3, SLC22A6, SLC22A 8, SLC22A 12, and AQP9;

(3) quantifying the RNA by a method selected from the group consisting of reverse-transcription polymerase chain reaction (RT-PCR), real-time RT-PCR, northern blotting, fluorescence activated cell sorting, ELISA, and mass spectrometry;

(4) comparing the amount of the RNA from the patient to the quantity of a corresponding RNA from individuals having normal kidney function, (5) determining a difference between the quantity of the RNA from the patient and the quantity of the corresponding RNA from the individuals having normal kidney function, wherein a difference in the quantity of the RNA between the patient and the individuals indicates a change in kidney function of the patient, and wherein a lack of a difference in the quantity of said RNA between the patient and the individuals indicates that the kidney function of the patient is normal; and (B) administering a pharmaceutical agent for (i) lowering blood glucose, (ii) lowering blood pressure, or (iii) reducing inflammation to the patient if the results of the laboratory assay indicate a change in kidney function of the patient.

2. The method of claim 1, further comprising centrifuging said sample to remove cellular debris prior to capturing the vesicles.

3. The method of claim 1, wherein the quantifying comprises amplifying the RNA using PCR.

4. The method of claim 1, wherein the RNA comprises poly(A)+RNA.

5. The method of claim 1, wherein the RNA is collected from a specific region of the kidney, and wherein the specific region of the kidney is selected from the group consisting of the glomerulus, the proximal tubule, and the distal tubule.

6. A method for administering a therapy to a subject based on the kidney function of the patient, the method comprising:

(A) having a first sample of urine from a patient sent to a laboratory, wherein the sample comprises vesicles comprising RNA, for the laboratory to perform an assay comprising the following steps:

(1) capturing the vesicles from the first urine sample, wherein the capturing comprises:

(a) loading at least a portion of the first sample of biological fluid into a sample loading region of a vesicle capture device;

(b) passing the sample from the sample loading region through a vesicle-capture material in the vesicle capture device, the vesicle-capture material comprising a plurality of layers of glass-like materials, thereby producing a supernatant, wherein the plurality of layers of glass-like materials comprises at least a first layer and a second layer of glassfiber; and (c) passing the supernatant to a sample receiving region of the vesicle capture device, wherein the passings result in capture of the vesicles from the sample on or in the vesicle-capture material, thereby capturing the vesicles;

(2) lysing the captured vesicles to release the RNA, wherein the RNA comprises one or more RNA selected from the group consisting of UMOD, vWF, MMP3, SLC22A6, SLC22A 8, SLC22A12, and AQP9;

(3) quantifying the RNA by a method selected from the group consisting of reverse-transcription polymerase chain reaction (RT-PCR), real-time RT-PCR, northern blotting, fluorescence activated cell sorting, ELISA, and mass spectrometry;

(4) comparing the amount of the RNA from the patient to the quantity of a corresponding RNA from individuals having normal kidney function, (5) determining a difference between the quantity of the RNA from the patient and the quantity of the corresponding RNA from the individuals having normal kidney function, wherein a difference in the quantity of the RNA between the patient and the individuals indicates a change in kidney function of the patient, and wherein a lack of a difference in the quantity of said RNA between the patient and the individuals indicates that the kidney function of the patient is normal; and (B) administering a pharmaceutical agent for (i) lowering blood pressure, (ii) lowering blood glucose, or (iii) reducing inflammation to the patient if the results of the laboratory assay indicate a change in kidney function of the patient.

7. A method for administering a therapy to a subject based on the kidney function of the patient, the method comprising:

(A) having a first sample of urine from a patient sent to a laboratory, wherein the sample comprises vesicles comprising RNA, for the laboratory to perform an assay comprising the following steps:

(1) capturing the vesicles from the first urine sample, wherein the capturing comprises:

(a) loading at least a portion of the first sample of biological fluid into a sample loading region of a vesicle capture device;

(b) passing the sample from the sample loading region through a vesicle-capture material in the vesicle capture device, the vesicle-capture material comprising a plurality of layers of glass-like materials, thereby producing a supernatant; and (c) passing the supernatant to a sample receiving region of the vesicle capture device, wherein the passings result in capture of the vesicles from the sample on or in the vesicle-capture material, thereby capturing the vesicles;

(2) lysing the captured vesicles to release the RNA, wherein the RNA comprises one or more RNA selected from the group consisting of UMOD, vWF, MMP3, SLC22A6, SLC22A 8, SLC22A 12, and AQP9;

(3) quantifying the RNA by a method selected from the group consisting of reverse-transcription polymerase chain reaction (RT-PCR), real-time RT-PCR, northern blotting, fluorescence activated cell sorting, ELISA, and mass spectrometry;

(4) comparing the amount of the RNA from the patient to the quantity of a corresponding RNA from individuals having normal kidney function, (5) determining a difference between the quantity of the RNA from the patient and the quantity of the corresponding RNA from the individuals having normal kidney function, wherein a difference in the quantity of the RNA between the patient and the individuals indicates a change in kidney function of the patient, and wherein a lack of a difference in the quantity of said RNA between the patient and the individuals indicates that the kidney function of the patient is normal; and (B) administering a pharmaceutical agent for (i) lowering blood pressure, (ii) lowering blood glucose, or (iii) reducing inflammation to the patient if the results of the laboratory assay indicate a change in kidney function of the patient.

* * * * *

UNITED STATES PATENT AND TRADEMARK OFFICE
CERTIFICATE OF CORRECTION

| | | |
|---|---|---|
| PATENT NO. | : 9,012,615 B2 | Page 1 of 1 |
| APPLICATION NO. | : 13/710237 | |
| DATED | : April 21, 2015 | |
| INVENTOR(S) | : Masato Mitsuhashi | |

It is certified that error appears in the above-identified patent and that said Letters Patent is hereby corrected as shown below:

On The Title Page

In column 2 (page 1, item 56) at line 26, under Other Publications, change "Acquaporin" to --Aquaporin--.

In column 2 (page 1, item 56) at line 27, under Other Publications, change "Archie" to --Arhiv,--.

In column 2 (page 1, item 56) at line 36, under Other Publications, change "[retreived" to --[retrieved--.

In column 2 (page 2, item 56) at line 6, under Other Publications, change "micropadicles" to --microparticles--.

In column 2 (page 2, item 56) at line 10, under Other Publications, change "[Retreived" to --[Retrieved--.

In The Specification

In column 8 at line 52, change "reabosrption" to --reabsorption--.

In columns 17-18 at line 48, change "umbillical" to --umbilical--.

In column 18 at line 63, change "and or" to --and/or--.

In column 20 at line 66, change "reabsorbtion" to --reabsorption--.

In The Claims

In column 33 at line 58 (approx.), in Claim 1, change "labatory" to --laboratory--.

In column 33 at line 58 (approx.), in Claim 1, after "to" insert --perform--.

In column 34 at line 66, in Claim 1, after "supernatant" insert --to a sample--.

Signed and Sealed this
Twenty-third Day of February, 2016

Michelle K. Lee
*Director of the United States Patent and Trademark Office*

SEQUENCE LISTING

<160> NUMBER OF SEQ ID NOS: 36

<210> SEQ ID NO 1
<211> LENGTH: 18
<212> TYPE: DNA
<213> ORGANISM: Homo sapiens
<220> FEATURE:
<221> NAME/KEY: misc_feature
<223> OTHER INFORMATION: Forward primer for beta-actin

<400> SEQUENCE: 1
cctggcaccc agcacaat                                                 18

-continued

```
<210> SEQ ID NO 2
<211> LENGTH: 20
<212> TYPE: DNA
<213> ORGANISM: Homo sapiens
<220> FEATURE:
<221> NAME/KEY: misc_feature
<223> OTHER INFORMATION: Reverse primer for beta-actin

<400> SEQUENCE: 2
gccgatccac acggagtact                                                   20

<210> SEQ ID NO 3
<211> LENGTH: 23
<212> TYPE: DNA
<213> ORGANISM: Homo sapiens
<220> FEATURE:
<221> NAME/KEY: misc_feature
<223> OTHER INFORMATION: Forward primer for beta-2 microglobulin

<400> SEQUENCE: 3
tgactttgtc acagcccaag ata                                               23

<210> SEQ ID NO 4
<211> LENGTH: 20
<212> TYPE: DNA
<213> ORGANISM: Homo sapiens
<220> FEATURE:
<221> NAME/KEY: misc_feature
<223> OTHER INFORMATION: Reverse primer for beta-2 microglobulin

<400> SEQUENCE: 4
aatgcggcat cttcaaacct                                                   20

<210> SEQ ID NO 5
<211> LENGTH: 23
<212> TYPE: DNA
<213> ORGANISM: Homo sapiens
<220> FEATURE:
<221> NAME/KEY: misc_feature
<223> OTHER INFORMATION: Forward primer for VWF

<400> SEQUENCE: 5
ccctgggtta caaggaagaa aat                                               23

<210> SEQ ID NO 6
<211> LENGTH: 26
<212> TYPE: DNA
<213> ORGANISM: Homo sapiens
<220> FEATURE:
<221> NAME/KEY: misc_feature
<223> OTHER INFORMATION: Reverse primer for VWF

<400> SEQUENCE: 6
agtgtcatga tctgtcctcc tcttag                                            26

<210> SEQ ID NO 7
<211> LENGTH: 26
<212> TYPE: DNA
<213> ORGANISM: Homo sapiens
<220> FEATURE:
<221> NAME/KEY: misc_feature
<223> OTHER INFORMATION: Forward primer for MMP1

<400> SEQUENCE: 7
cggtttttca aagggaataa gtactg                                            26

<210> SEQ ID NO 8
```

```
<211> LENGTH: 24
<212> TYPE: DNA
<213> ORGANISM: Homo sapiens
<220> FEATURE:
<221> NAME/KEY: misc_feature
<223> OTHER INFORMATION: Reverse primer for MMP1

<400> SEQUENCE: 8
gaagccaaag gagctgtaga tgtc                                              24

<210> SEQ ID NO 9
<211> LENGTH: 23
<212> TYPE: DNA
<213> ORGANISM: Homo sapiens
<220> FEATURE:
<221> NAME/KEY: misc_feature
<223> OTHER INFORMATION: Forward primer for MMP3

<400> SEQUENCE: 9
tcccaagcaa atagctgaag act                                               23

<210> SEQ ID NO 10
<211> LENGTH: 23
<212> TYPE: DNA
<213> ORGANISM: Homo sapiens
<220> FEATURE:
<221> NAME/KEY: misc_feature
<223> OTHER INFORMATION: Reverse primer for MMP3

<400> SEQUENCE: 10
ttctttgcat ttgggtcaaa ctc                                               23

<210> SEQ ID NO 11
<211> LENGTH: 18
<212> TYPE: DNA
<213> ORGANISM: Homo sapiens
<220> FEATURE:
<221> NAME/KEY: misc_feature
<223> OTHER INFORMATION: Forward primer for REN

<400> SEQUENCE: 11
gtgcacactg gccatcca                                                     18

<210> SEQ ID NO 12
<211> LENGTH: 26
<212> TYPE: DNA
<213> ORGANISM: Homo sapiens
<220> FEATURE:
<221> NAME/KEY: misc_feature
<223> OTHER INFORMATION: Reverse primer for REN

<400> SEQUENCE: 12
aaactctgtg tagaactttc ggatga                                            26

<210> SEQ ID NO 13
<211> LENGTH: 25
<212> TYPE: DNA
<213> ORGANISM: Homo sapiens
<220> FEATURE:
<221> NAME/KEY: misc_feature
<223> OTHER INFORMATION: Forward primer for SLC12A1

<400> SEQUENCE: 13
actccagagc tgctaatctc attgt                                             25

<210> SEQ ID NO 14
<211> LENGTH: 26
```

```
<212> TYPE: DNA
<213> ORGANISM: Homo sapiens
<220> FEATURE:
<221> NAME/KEY: misc_feature
<223> OTHER INFORMATION: Reverse primer for SLC12A1

<400> SEQUENCE: 14
aactagtaag acaggtggga ggttct                                          26

<210> SEQ ID NO 15
<211> LENGTH: 19
<212> TYPE: DNA
<213> ORGANISM: Homo sapiens
<220> FEATURE:
<221> NAME/KEY: misc_feature
<223> OTHER INFORMATION: Forward primer for SLC22A6

<400> SEQUENCE: 15
acaatgatcc gcgctgtca                                                  19

<210> SEQ ID NO 16
<211> LENGTH: 20
<212> TYPE: DNA
<213> ORGANISM: Homo sapiens
<220> FEATURE:
<221> NAME/KEY: misc_feature
<223> OTHER INFORMATION: Reverse primer for SLC22A6

<400> SEQUENCE: 16
gtcgcgtctg tttccctttc                                                 20

<210> SEQ ID NO 17
<211> LENGTH: 28
<212> TYPE: DNA
<213> ORGANISM: Homo sapiens
<220> FEATURE:
<221> NAME/KEY: misc_feature
<223> OTHER INFORMATION: Forward primer for SLC22A8

<400> SEQUENCE: 17
tctacacaag tgaattatac cccacagt                                        28

<210> SEQ ID NO 18
<211> LENGTH: 19
<212> TYPE: DNA
<213> ORGANISM: Homo sapiens
<220> FEATURE:
<221> NAME/KEY: misc_feature
<223> OTHER INFORMATION: Reverse primer for SLC22A8

<400> SEQUENCE: 18
cgcgggtcca caggttact                                                  19

<210> SEQ ID NO 19
<211> LENGTH: 22
<212> TYPE: DNA
<213> ORGANISM: Homo sapiens
<220> FEATURE:
<221> NAME/KEY: misc_feature
<223> OTHER INFORMATION: Forward primer for SLC22A12

<400> SEQUENCE: 19
ggacctgtat ctccacgttg tg                                              22

<210> SEQ ID NO 20
<211> LENGTH: 22
<212> TYPE: DNA
```

```
<213> ORGANISM: Homo sapiens
<220> FEATURE:
<221> NAME/KEY: misc_feature
<223> OTHER INFORMATION: Reverse primer for SLC22A12

<400> SEQUENCE: 20
gatgtccacg acaccaatga ac                                             22

<210> SEQ ID NO 21
<211> LENGTH: 20
<212> TYPE: DNA
<213> ORGANISM: Homo sapiens
<220> FEATURE:
<221> NAME/KEY: misc_feature
<223> OTHER INFORMATION: Forward primer for UMOD

<400> SEQUENCE: 21
cctgaacttg ggtcccatca                                                20

<210> SEQ ID NO 22
<211> LENGTH: 19
<212> TYPE: DNA
<213> ORGANISM: Homo sapiens
<220> FEATURE:
<221> NAME/KEY: misc_feature
<223> OTHER INFORMATION: Reverse primer for UMOD

<400> SEQUENCE: 22
gccccaagct gctaaaagc                                                 19

<210> SEQ ID NO 23
<211> LENGTH: 22
<212> TYPE: DNA
<213> ORGANISM: Homo sapiens
<220> FEATURE:
<221> NAME/KEY: misc_feature
<223> OTHER INFORMATION: Forward primer for SPP1

<400> SEQUENCE: 23
agccaatgat gagagcaatg ag                                             22

<210> SEQ ID NO 24
<211> LENGTH: 21
<212> TYPE: DNA
<213> ORGANISM: Homo sapiens
<220> FEATURE:
<221> NAME/KEY: misc_feature
<223> OTHER INFORMATION: Reverse primer for SPP1

<400> SEQUENCE: 24
tggaattcac ggctgacttt g                                              21

<210> SEQ ID NO 25
<211> LENGTH: 20
<212> TYPE: DNA
<213> ORGANISM: Homo sapiens
<220> FEATURE:
<221> NAME/KEY: misc_feature
<223> OTHER INFORMATION: Forward primer for ALB

<400> SEQUENCE: 25
tgcaaggctg acgataagga                                                20

<210> SEQ ID NO 26
<211> LENGTH: 26
<212> TYPE: DNA
<213> ORGANISM: Homo sapiens
```

```
<220> FEATURE:
<221> NAME/KEY: misc_feature
<223> OTHER INFORMATION: Reverse primer for ALB

<400> SEQUENCE: 26
gtaggctgag atgcttttaa atgtga                                              26

<210> SEQ ID NO 27
<211> LENGTH: 22
<212> TYPE: DNA
<213> ORGANISM: Homo sapiens
<220> FEATURE:
<221> NAME/KEY: misc_feature
<223> OTHER INFORMATION: Forward primer for podocin

<400> SEQUENCE: 27
aggatggcag ctgagattct gt                                                  22

<210> SEQ ID NO 28
<211> LENGTH: 24
<212> TYPE: DNA
<213> ORGANISM: Homo sapiens
<220> FEATURE:
<221> NAME/KEY: misc_feature
<223> OTHER INFORMATION: Reverse primer for podocin

<400> SEQUENCE: 28
agagactgaa gggtgtggag gtat                                                24

<210> SEQ ID NO 29
<211> LENGTH: 21
<212> TYPE: DNA
<213> ORGANISM: Homo sapiens
<220> FEATURE:
<221> NAME/KEY: misc_feature
<223> OTHER INFORMATION: Forward primer for nephrin

<400> SEQUENCE: 29
cttccctggg cacttgtatg a                                                   21

<210> SEQ ID NO 30
<211> LENGTH: 25
<212> TYPE: DNA
<213> ORGANISM: Homo sapiens
<220> FEATURE:
<221> NAME/KEY: misc_feature
<223> OTHER INFORMATION: Reverse primer for nephrin

<400> SEQUENCE: 30
tcatagattc ctcttggatc ctgat                                               25

<210> SEQ ID NO 31
<211> LENGTH: 19
<212> TYPE: DNA
<213> ORGANISM: Homo sapiens
<220> FEATURE:
<221> NAME/KEY: misc_feature
<223> OTHER INFORMATION: Forward primer for cubulin

<400> SEQUENCE: 31
ccggctatcc aggcacata                                                      19

<210> SEQ ID NO 32
<211> LENGTH: 20
<212> TYPE: DNA
<213> ORGANISM: Homo sapiens
<220> FEATURE:
```

```
<221> NAME/KEY: misc_feature
<223> OTHER INFORMATION: Reverse primer for cubulin

<400> SEQUENCE: 32
ccttccagca ggagcaacaa                                              20

<210> SEQ ID NO 33
<211> LENGTH: 21
<212> TYPE: DNA
<213> ORGANISM: Homo sapiens
<220> FEATURE:
<221> NAME/KEY: misc_feature
<223> OTHER INFORMATION: Forward primer for low density lipoprotein
      receptor related protein 2

<400> SEQUENCE: 33
gcacagatgg agaacgagca a                                            21

<210> SEQ ID NO 34
<211> LENGTH: 19
<212> TYPE: DNA
<213> ORGANISM: Homo sapiens
<220> FEATURE:
<221> NAME/KEY: misc_feature
<223> OTHER INFORMATION: Reverse primer for low density lipoprotein
      receptor related protein 2

<400> SEQUENCE: 34
agcagggagc gaaggtgat                                               19

<210> SEQ ID NO 35
<211> LENGTH: 25
<212> TYPE: DNA
<213> ORGANISM: Homo sapiens
<220> FEATURE:
<221> NAME/KEY: misc_feature
<223> OTHER INFORMATION: Forward primer for aquaporin 9

<400> SEQUENCE: 35
aaacaacttc tggtggattc ctgta                                        25

<210> SEQ ID NO 36
<211> LENGTH: 21
<212> TYPE: DNA
<213> ORGANISM: Homo sapiens
<220> FEATURE:
<221> NAME/KEY: misc_feature
<223> OTHER INFORMATION: Reverse primer for aquaporin 9

<400> SEQUENCE: 36
gctctggatg gtggatttca a                                            21
```